US011655133B2

(12) United States Patent
Hayakawa et al.

(10) Patent No.: US 11,655,133 B2
(45) Date of Patent: May 23, 2023

(54) CAP STERILIZER, CONTENT FILLING SYSTEM, CAP STERILIZATION METHOD, AND CONTENT FILLING METHOD

(71) Applicant: DAI NIPPON PRINTING CO., LTD., Tokyo-to (JP)

(72) Inventors: Atsushi Hayakawa, Tokyo-to (JP); Masatoshi Takagi, Tokyo-to (JP); Hitoshi Takaku, Tokyo-to (JP)

(73) Assignee: DAI NIPPON PRINTING CO., LTD., Tokyo (JP)

( * ) Notice: Subject to any disclaimer, the term of this patent is extended or adjusted under 35 U.S.C. 154(b) by 1 day.

(21) Appl. No.: 17/196,333

(22) Filed: Mar. 9, 2021

(65) Prior Publication Data
US 2021/0188611 A1    Jun. 24, 2021

Related U.S. Application Data

(62) Division of application No. 16/306,527, filed as application No. PCT/JP2017/020279 on May 31, 2017, now Pat. No. 10,974,941.

(30) Foreign Application Priority Data

May 31, 2016  (JP) ............................. JP2016-109230
Jun. 17, 2016  (JP) ............................. JP2016-120994
(Continued)

(51) Int. Cl.
*B67C 7/00*    (2006.01)
*B65B 55/10*   (2006.01)
(Continued)

(52) U.S. Cl.
CPC ............. *B67C 7/0073* (2013.01); *A61L 2/18* (2013.01); *A61L 2/20* (2013.01); *A61L 2/208* (2013.01);
(Continued)

(58) Field of Classification Search
CPC ....... B67B 3/003; B67C 7/004; B67C 7/0073; B67C 7/0086; B65B 55/10; B65B 55/04;
(Continued)

(56) References Cited

U.S. PATENT DOCUMENTS 8,291,680 B2    10/2012  Silvestri
8,931,239 B2 *  1/2015   Evers ...................... B67B 3/003
                                                    53/306
(Continued)

FOREIGN PATENT DOCUMENTS

CN        1547540 A      11/2004
CN      102145186 A       8/2011
(Continued)

OTHER PUBLICATIONS

Jan. 4, 2022 European Office Action issued in European Application No. 17806736.9.
(Continued)

*Primary Examiner* — Stephen F. Gerrity
(74) *Attorney, Agent, or Firm* — Oliff PLC

(57) ABSTRACT

A cap sterilizer (50) includes an infeed chamber (52), a sterilant atomizing chamber (53), and an air rinse chamber (54). At least the infeed chamber (52) and the air rinse chamber (54) are exhausted. Both an exhaust pressure (E2) in the infeed chamber (52) and an exhaust pressure (E4) in the air rinse chamber are higher than an exhaust pressure (E3) in the sterilant atomizing chamber (53), or the sterilant atomizing chamber (53) is not exhausted.

6 Claims, 14 Drawing Sheets

(30) Foreign Application Priority Data

| | | | |
|---|---|---|---|
| Jun. 17, 2016 | (JP) | ............................ | JP2016-121000 |
| Jul. 28, 2016 | (JP) | ............................ | JP2016-148789 |
| Jul. 28, 2016 | (JP) | ............................ | JP2016-148802 |
| Jul. 28, 2016 | (JP) | ............................ | JP2016-148813 |
| Jul. 28, 2016 | (JP) | ............................ | JP2016-148817 |
| Feb. 3, 2017 | (JP) | ............................ | JP2017-018936 |

(51) Int. Cl.
  *B67B 3/00* (2006.01)
  *A61L 2/18* (2006.01)
  *A61L 2/20* (2006.01)

(52) U.S. Cl.
  CPC .............. *B65B 55/10* (2013.01); *B67B 3/003* (2013.01); *B67C 7/004* (2013.01); *A61L 2202/20* (2013.01)

(58) Field of Classification Search
  CPC ...... A61L 2/186; A61L 2/208; A61L 2202/20; A61L 2202/23
  USPC ......................................................... 53/426
  See application file for complete search history.

(56) References Cited

U.S. PATENT DOCUMENTS

| | | | |
|---|---|---|---|
| 8,945,477 B2 | 2/2015 | Ceci et al. | |
| 10,974,941 B2 * | 4/2021 | Hayakawa et al. | B67B 3/003 |
| 2004/0208781 A1 | 10/2004 | Hayashi et al. | |
| 2005/0169796 A1 * | 8/2005 | Krakers et al. | B67B 3/003 |
| | | | 422/302 |
| 2007/0006550 A1 | 1/2007 | Kemper et al. | |
| 2008/0107562 A1 | 5/2008 | Hayashi et al. | |
| 2011/0311399 A1 * | 12/2011 | Silvestri et al. | A61L 2/208 |
| | | | 422/292 |
| 2014/0318083 A1 | 10/2014 | Marastoni | |
| 2015/0246801 A1 | 9/2015 | Niehr et al. | |

FOREIGN PATENT DOCUMENTS

| | | | | |
|---|---|---|---|---|
| DE | 102010032601 A1 * | 2/2012 | ............. | B65B 55/10 |
| EP | 824974 A1 * | 2/1998 | ............. | A61L 2/183 |
| EP | 1749747 A1 | 2/2007 | | |
| JP | S59-127632 U | 8/1984 | | |
| JP | S61-3684 A | 1/1986 | | |
| JP | S62-38223 B2 | 8/1987 | | |
| JP | S6238223 B2 * | 8/1987 | | |
| JP | S63-178926 A | 7/1988 | | |
| JP | 01182225 A * | 7/1989 | | |
| JP | 02004624 A * | 1/1990 | | |
| JP | H04-55936 A | 2/1992 | | |
| JP | H05-338629 A | 12/1993 | | |
| JP | H06-293319 A | 10/1994 | | |
| JP | H07-98534 B2 | 10/1995 | | |
| JP | 10152115 A * | 6/1998 | | |
| JP | H10-152115 A | 6/1998 | | |
| JP | H10-258812 A | 9/1998 | | |
| JP | H11-193009 A | 7/1999 | | |
| JP | 11342917 A | 12/1999 | | |
| JP | 3909734 B2 | 2/2000 | | |
| JP | 2002-507176 A | 3/2002 | | |
| JP | 2002-104332 A | 4/2002 | | |
| JP | 2002104332 A * | 4/2002 | | |
| JP | 2003-128023 A | 5/2003 | | |
| JP | 2006-111295 A | 4/2006 | | |
| JP | 2009-107633 A | 5/2009 | | |
| JP | 2011-11811 A | 1/2011 | | |
| JP | 2011-162220 A | 8/2011 | | |
| JP | 2012-500759 A | 1/2012 | | |
| JP | 2013-133152 A | 7/2013 | | |
| JP | 2013-133153 A | 7/2013 | | |
| JP | 2014-15265 A | 1/2014 | | |
| JP | 2014-51293 A | 3/2014 | | |
| JP | 2015-85964 A | 5/2015 | | |
| JP | 2015-116815 A | 6/2015 | | |
| JP | 2015-157651 A | 9/2015 | | |
| JP | 2015-217951 A | 12/2015 | | |
| JP | 2016-84138 A | 5/2016 | | |
| JP | 2016-94224 A | 5/2016 | | |
| JP | 2016094224 A * | 5/2016 | | |
| JP | 6056930 B1 | 1/2017 | | |
| WO | 03/022689 A1 | 3/2003 | | |
| WO | 2010/024165 A1 | 3/2010 | | |

OTHER PUBLICATIONS

Sep. 18, 2020 Office Action issued in Japanese Patent Application No. 2019-127022.
Sep. 18, 2020 Office Action issued in Japanese Patent Application No. 2019-127044.
Sep. 18, 2020 Office Action issued in Japanese Patent Application No. 2019-127096.
Jul. 23, 2019 Office Action issued in Japanese Patent Application No. 2018-160786.
Mar. 12, 2019 Office Action issued in Japanese Patent Application No. 2018-025141.
Mar. 12, 2019 Office Action issued in Japanese Patent Application No. 2018-025142.
Mar. 15, 2019 Office Action issued in Japanese Patent Application No. 2018-025121.
Mar. 15, 2019 Office Action issued in Japanese Patent Application No. 2018-025136.
Mar. 15, 2019 Office Action issued in Japanese Patent Application No. 2018-025147.
Aug. 29, 2017 International Search Report issued in International Patent Application No. PCT/JP2017/020279.
Dec. 4, 2018 International Preliminary Report on Patentability issued in International Patent Application No. PCT/JP2017/020279.
Jun. 27, 2017 Office Action issued in Japanese Patent Application No. 2016-109230.
Jun. 27, 2017 Office Action issued in Japanese Patent Application No. 2016-121000.
Jun. 27, 2017 Office Action issued in Japanese Patent Application No. 2016-120994.
Jan. 12, 2018 Office Action issued in Japanese Patent Application No. 2016-120994.
Jun. 27, 2017 Office Action issued in Japanese Patent Application No. 2016-148817.
Jan. 12, 2018 Office Action issued in Japanese Patent Application No. 2016-148817.
Jun. 27, 2017 Office Action issued in Japanese Patent Application No. 2016-148789.
Jun. 27, 2017 Office Action issued in Japanese Patent Application No. 2016-148802.
Jun. 27, 2017 Office Action issued in Japanese Patent Application No. 2016-148813.
Apr. 27, 2018 Office Action issued in Japanese Patent Application No. 2017-018936.
Oct. 23, 2018 Office Action issued in Japanese Patent Application No. 2017-018936.
Mar. 3, 2020 Office Action issued in Japanese Patent Application No. 2018-160786.
Jun. 11, 2019 Office Action issued in Japanese Patent Application No. 2018-025121.
Jun. 11, 2019 Office Action issued in Japanese Patent Application No. 2018-025136.
Feb. 28, 2020 Search Report issued in European Patent Application No. 17806736.9.
Apr. 9, 2020 Office Action issued in Indonesian Patent Application No. P-00201810800.
Jun. 30, 2020 Office Action issued in Chinese Patent Application No. 201780031424.6.
Oct. 19, 2022 Search Report issued in European Patent Application No. 22187439.9.

* cited by examiner

CAP STERILIZER, CONTENT FILLING SYSTEM, CAP STERILIZATION METHOD, AND CONTENT FILLING METHOD

This application is a divisional application of U.S. patent application Ser. No. 16/306,527, filed Nov. 30, 2018, which is a National Stage of International Application No. PCT/JP2017/020279, filed May 31, 2017, which claims priority to Japanese Patent Applications No. 2017-018936, filed Feb. 3, 2017, No. 2016-148789, filed Jul. 28, 2016, No. 2016-148802, filed Jul. 28, 2016, No. 2016-109230, file May 31, 2016, No. 2016-148817, Jul. 28, 2016, No. 2016-120994, filed Jun. 17, 2016, No. 2016-121000, filed Jun. 17, 2016, and No. 2016-148813, filed Jul. 28, 2016. The disclosures of the prior applications are hereby incorporated by reference herein in their entireties.

TECHNICAL FIELD

The present invention relates to a cap sterilizer, a content filling system, a cap sterilization method and a content filling method.

BACKGROUND ART

A sterile filling system (aseptic filling system) has been known in which a sterilized content is filled inside a sterilized container (PET bottle) in a sterile environment and then the container is capped with a cap. Specifically, in the sterile filling system, a molded container is fed to the sterile filling system, and a hydrogen peroxide aqueous solution as a sterilant is sprayed on the container in the sterile filling system. After that, the container is dried and sterilized, and then, a content is aseptically filled inside the container. As another method, there is a method of adding dropwise a small amount of sterilant on an inner surface of a container at the time of molding the container, sealing a mouth to sterilize the inner surface of the container with vapor of the vaporized sterilant (hydrogen peroxide), feeding the sterilized container to a sterile filling system, sterilizing an outer surface of the container in the sterile filling system, and then opening the mouth to aseptically fill the content.

In such a sterile filling system, when a content is filled in a container, and seaming is performed with a cap to produce a product, it is necessary to sterilize the cap as well as the container. As such a cap sterilizer for sterilizing a cap, those described in Patent Literatures 1 to 3 are known, for example.

However, in the conventional cap sterilizers, there is a problem that it is difficult to increase the conveying speed of a cap. If the conveying speed of the cap is increased in the conventional cap sterilizers, the sterilization effect on an outer surface of the cap may be deteriorated. In addition, if the conveying speed of the cap is to be increased, there are problems that the cap sterilizer becomes large, the cost of capital investment increases, and the cost of medicine, thermal energy or washing water required for sterilization increases. Furthermore, in recent years, various caps such as a light-weight cap and a cap for carbonated drinks have been used in a sterile filling system, and in addition to sterilization in a short time, controlling a cap seaming angle and a torque within a specified range is required, for example.

CITATION LIST

Patent Literature

Patent Literature 1: JP 6-293319 A
Patent Literature 2: JP 2011-11811 A
Patent Literature 3: JP 2012-500759 A The present invention has been made in view of these circumstances, and an object of the present invention is to provide a cap sterilizer capable of reliably sterilizing a cap even when the conveying speed of the cap increases, a content filling system, a cap sterilization method, and a content filling method. Another object of the present invention is to provide a cap sterilizer capable of increasing the conveying speed of a cap, a content filling system, a cap sterilization method, and a content filling method.

SUMMARY OF INVENTION

The present invention is a cap sterilizer, and the cap sterilizer includes an infeed chamber, a sterilant atomizing chamber which sprays a sterilant against a cap fed from the infeed chamber, and an air rinse chamber which air-rinses the cap sprayed with the sterilant in the sterilant atomizing chamber. In this cap sterilizer, the infeed chamber, the sterilant atomizing chamber, and the air rinse chamber are arranged in this order along a conveying direction of the cap, at least the infeed chamber and the air rinse chamber are exhausted, and an exhaust pressure in the infeed chamber and an exhaust pressure in the air rinse chamber are higher than an exhaust pressure in the sterilant atomizing chamber, or the sterilant atomizing chamber is not exhausted.

In the cap sterilizer of the present invention, the exhaust pressure in the air rinse chamber is higher than the exhaust pressure in the infeed chamber.

The present invention is a cap sterilizer further including a washing chamber which washes the cap air-rinsed in the air rinse chamber, and in the cap sterilizer, the exhaust pressure in the washing chamber is higher than the exhaust pressure in the infeed chamber.

In the cap sterilizer of the present invention, a conveying speed of the cap is 100 cpm or more and 1500 cpm or less.

The present invention is a content filling system including the cap sterilizer.

The present invention is a cap sterilization method, and the cap sterilization method includes a step of feeding a cap from an infeed chamber to a sterilant atomizing chamber, a step of spraying a sterilant against the cap in the sterilant atomizing chamber, and a step of air-rinsing the cap, sprayed with the sterilant in the sterilant atomizing chamber, in an air rinse chamber. In this cap sterilization method, the infeed chamber, the sterilant atomizing chamber, and the air rinse chamber are arranged in this order along a conveying direction of the cap, at least the infeed chamber and the air rinse chamber are exhausted, and an exhaust pressure in the infeed chamber and an exhaust pressure in the air rinse chamber are higher than an exhaust pressure in the sterilant atomizing chamber, or the sterilant atomizing chamber is not exhausted.

The present invention is a cap sterilizer, and the cap sterilizer includes a first infeed chamber into which a cap is introduced, a second infeed chamber into which hot air is sent, and a sterilant atomizing chamber which sprays a sterilant against the cap fed from the second infeed chamber. In this cap sterilizer, the first infeed chamber, the second infeed chamber, and the sterilant atomizing chamber are arranged in this order along a conveying direction of the cap, and the first infeed chamber and the second infeed chamber are separated from each other by a partition wall.

The present invention is a cap sterilizer further including an air rinse chamber which air-rinses the cap sprayed with the sterilant in the sterilant atomizing chamber.

In the cap sterilizer of the present invention, an internal pressure of the first infeed chamber is maintained at −100 Pa or more and 10 Pa or less.

In the cap sterilizer of the present invention, an internal pressure of the second infeed chamber is maintained at 50 Pa or more and 200 Pa or less.

In the cap sterilizer of the present invention, a conveying speed of the cap is 100 cpm or more and 1500 cpm or less.

The present invention is a content filling system including the cap sterilizer.

The present invention is a cap sterilizer, and the cap sterilizer includes an infeed chamber and a sterilant atomizing chamber which sprays a sterilant against a cap fed from the infeed chamber. In this cap sterilizer, the sterilant atomizing chamber includes a spray nozzle which sprays the sterilant and a cover which covers surroundings of the spray nozzle.

In the cap sterilizer of the present invention, the sterilant atomizing chamber includes a rotation conveyance mechanism which conveys the cap while rotating, and the cover has a fan or arc-shape as viewed from the front side.

In the cap sterilizer of the present invention, the spray nozzle includes a spray nozzle for outer surface which supplies the sterilant to an outer surface side of the cap and a spray nozzle for inner surface which supplies the sterilant to an inner surface side of the cap, and the spray nozzle for outer surface is located downstream of the spray nozzle for inner surface in the conveying direction of the cap.

In the cap sterilizer of the present invention, a washing nozzle which ejects a washing liquid toward an interior of the cover is provided inside the cover.

In the cap sterilizer of the present invention, a conveying speed of the cap is 100 cpm or more and 1500 cpm or less.

The present invention is a content filling system including the cap sterilizer.

The present invention is a cap sterilizer, and the cap sterilizer includes a spray nozzle which sprays a sterilant against a cap and an air rinse nozzle which air-rinses the cap sprayed with the sterilant by the spray nozzle. In this cap sterilizer, sterile hot air is blown against both inner and outer surfaces of the cap by the air rinse nozzle.

In the cap sterilizer of the present invention, as the sterile hot air is blown by the air rinse nozzle, temperature of the cap rises to 40° C. or more.

The present invention is a cap sterilizer further including a washing nozzle which washes the cap air-rinsed by the air rinse nozzle.

In the cap sterilizer of the present invention, a conveying speed of the cap is 100 cpm or more and 1500 cpm or less.

The present invention is a content filling system including the cap sterilizer.

The present invention is a cap sterilization method, and the cap sterilization method includes a step of spraying a sterilant against a cap and a step of air-rinsing the cap sprayed with the sterilant. In this cap sterilization method, sterile hot air is blown against both inner and outer surfaces of the cap in the air-rinsing step.

The present invention is a cap sterilizer, and the cap sterilizer includes a spray nozzle which sprays a sterilant against a cap, an air-rinse nozzle which air-rinses the cap sprayed with the sterilant by the spray nozzle, and a washing nozzle which washes the cap air-rinsed by the air rinse nozzle. In this cap sterilizer, the spray nozzle, the air rinse nozzle, and the washing nozzle are arranged in this order along a conveying direction of the cap, and a washing liquid is blown against the cap by the washing nozzle to wash the cap.

The present invention is a cap sterilizer further including an air blow nozzle which blows air against the cap to remove the washing liquid adhering to the cap.

In the cap sterilizer of the present invention, a conveying speed of the cap is 100 cpm or more and 1500 cpm or less.

The present invention is a content filling system including the cap sterilizer.

The present invention is a cap sterilization method, and the cap sterilization method includes a step of spraying a sterilant against a cap, a step of air-rinsing the cap sprayed with the sterilant, and a step of washing the air-rinsed cap. In this cap sterilization method, in the washing step, a washing liquid is blown against the cap to wash the cap.

The present invention is a cap sterilization method further including a step of blowing air against the cap to remove the washing liquid adhering to the cap.

In the cap sterilization method of the present invention, when air is blown against the cap, a part of the washing liquid adhering to the cap is left.

The present invention is a cap sterilizer, and the cap sterilizer includes a sterilant atomizing chamber which sprays a sterilant against a cap and an air rinse chamber which air-rinses the cap sprayed with the sterilant in the sterilant atomizing chamber. In this cap sterilizer, sterile hot air is blown against both inner and outer surfaces of the cap in the air rinse chamber.

In the cap sterilizer of the present invention, as the sterile hot air is blown in the air rinse chamber, temperature of the cap rises to 40° C. or more.

The present invention is a cap sterilizer further including a washing chamber which washes the cap air-rinsed in the air rinse chamber.

In the cap sterilizer of the present invention, a conveying speed of the cap is 100 cpm or more and 1500 cpm or less.

The present invention is a content filling system including the cap sterilizer.

The present invention is a cap sterilization method, and the cap sterilization method includes a step of feeding a cap to a sterilant atomizing chamber, a step of spraying a sterilant against the cap in the sterilant atomizing chamber, and a step of air-rinsing the cap, sprayed with the sterilant in the sterilant atomizing chamber, in an air rinse chamber. In this cap sterilization method, sterile hot air is blown against both inner and outer surfaces of the cap in the air rinse chamber.

The present invention is a cap sterilizer, and the cap sterilizer includes a sterilant atomizing chamber which sprays a sterilant against a cap, an air rinse chamber which air-rinses the cap sprayed with the sterilant in the sterilant atomizing chamber, and a washing chamber which washes the cap air-rinsed in the air rinse chamber. In this cap sterilizer, the sterilant atomizing chamber, the air rinse chamber, and the washing chamber are arranged in this order along a conveying direction of the cap, and in the washing chamber, a washing liquid is blown against the cap to wash the cap.

In the cap sterilizer of the present invention, air is blown against the cap in the washing chamber to remove the washing liquid adhering to the cap.

In the cap sterilizer of the present invention, a conveying speed of the cap is 100 cpm or more and 1500 cpm or less.

The present invention is a content filling system including the cap sterilizer.

The present invention is a cap sterilization method, and the cap sterilization method includes a step of spraying a sterilant against a cap in a sterilant atomizing chamber, a step of air-rinsing the cap, sprayed with the sterilant in the sterilant atomizing chamber, in an air rinse chamber, and a step of washing the cap, air-rinsed in the air rinse chamber, in a washing chamber. In this cap sterilization method, the sterilant atomizing chamber, the air rinse chamber, and the washing chamber are arranged in this order along a conveying direction of the cap, and in the washing chamber, a washing liquid is blown against the cap to wash the cap.

In the cap sterilization method of the present invention, air is blown against the cap in the washing chamber to remove the washing liquid adhering to the cap.

In the cap sterilization method of the present invention, when air is blown against the cap, a part of the washing liquid adhering to the cap is left.

The present invention is a cap sterilizer, and the cap sterilizer includes a sterilant atomizing wheel, which conveys a cap while rotating and sprays a sterilant against the cap being conveyed, and an air rinse wheel which conveys the cap, sprayed with the sterilant in the sterilant atomizing wheel, while rotating and air-rinses the cap being conveyed.

In the cap sterilizer of the present invention, the sterilant atomizing wheel has a rotating mechanism which conveys the cap while rotating and a spray nozzle which blows a sterilant against the cap rotated and conveyed by the rotating mechanism.

In the cap sterilizer of the present invention, the sterilant atomizing wheel further has a supply spray which supplies a sterilant and a heater which heats the sterilant from the supply spray, and the sterilant heated by the heater is supplied to the spray nozzle.

The present invention is a content filling system, and the content filling system includes a bottle sterilizer which sterilizes a bottle, a filling device which fills a content into the bottle, the cap sterilizer, and a cap attachment device which attaches the cap, delivered from the cap sterilizer, to a mouth of the bottle filled with the content by the filling device.

In the content filling system of the present invention, both the cap sterilizer and the cap attachment device are disposed in a sterile chamber.

In the content filling system of the present invention, the bottle sterilizer, the filling device, the cap sterilizer, and the cap attachment device are connected to each other by a wheel and disposed in a sterile chamber.

The present invention is a cap sterilization method, and the cap sterilization method includes a sterilant spray step of conveying a cap while rotating the cap by a sterilant atomizing wheel and spraying a sterilant against the cap being conveyed and an air-rinsing step of conveying the cap, sprayed with the sterilant, while rotating the cap by the air rinse wheel and air-rinsing the cap being conveyed.

The present invention is a content filling method, and the content filling method includes a bottle sterilization step of sterilizing a bottle by a bottle sterilizer, a filling step of filling the bottle with a content by a filling device, a sterilant spray step of conveying a cap while rotating the cap by a sterilant atomizing wheel of a cap sterilizer and spraying a sterilant against the cap being conveyed, an air-rinsing step of conveying the cap, sprayed with the sterilant, while rotating the cap by an air rinse wheel of the cap sterilizer and air-rinsing the cap being conveyed, and a cap attachment step of attaching the sterilized cap to a mouth of the bottle by a cap attachment device.

In the content filling method of the present invention, the bottle sterilizer, the filling device, the cap sterilizer, and the cap attachment device are connected to each other by a wheel and disposed in a sterile chamber.

According to the present invention, even when the conveying speed of the cap increases, the cap can be reliably sterilized.

According to the present invention, it is possible to increase the conveying speed of the cap. Since the cap sterilizer is disposed in the sterile chamber, there is no need to provide a dedicated sterile chamber for cap sterilization.

DESCRIPTION OF EMBODIMENTS

First Embodiment

Figure 1:
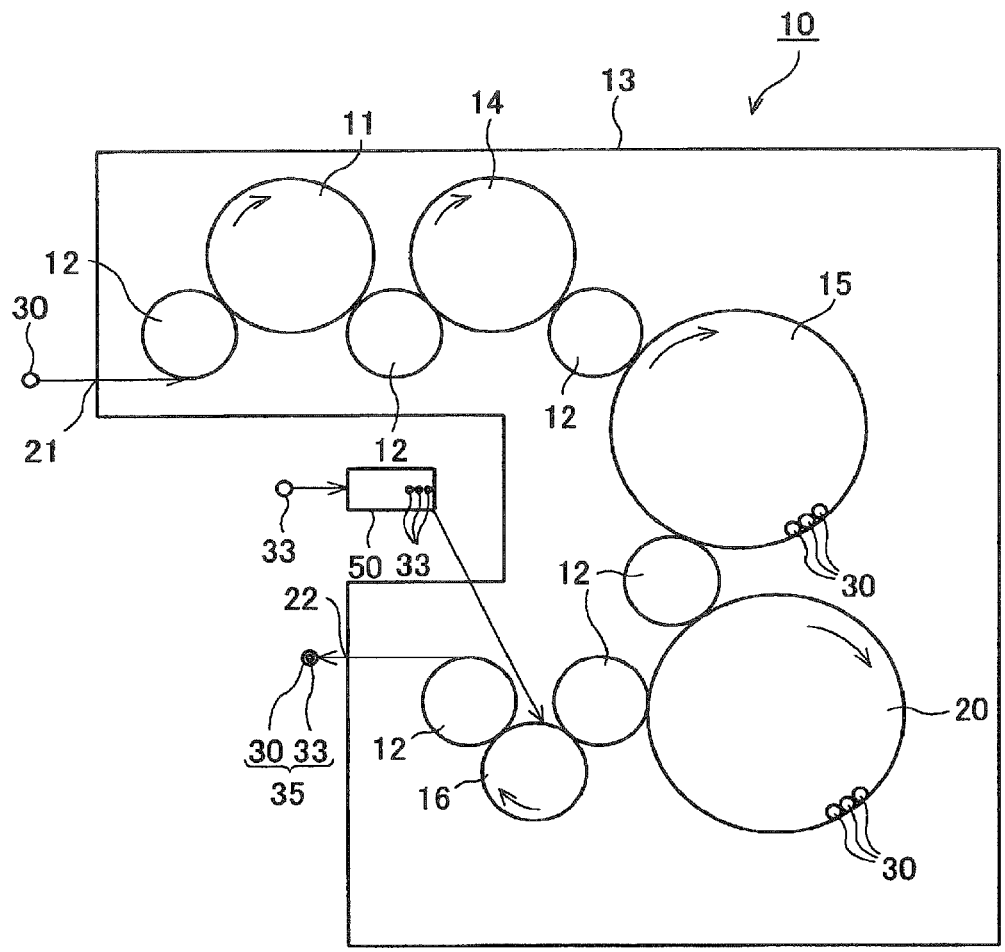
FIG. 1 is a schematic plan view illustrating a content filling system according to a first embodiment of the present invention.

A first embodiment of the present invention will be described below with reference to FIGS. 1 to 6. FIGS. 1 to 6 illustrate one embodiment of the present invention. In the following drawings, the same reference numerals are assigned to the same components, and some detailed descriptions may be omitted.

(Content Filling System)

First, a content filling system (sterile filling system, aseptic filling system) according to the present embodiment will be described with reference to FIG. 1.

A content filling system 10 illustrated in FIG. 1 is a system for filling a bottle (container) 30 with a content such as a beverage. The bottle 30 can be made by performing biaxial stretching blow molding on a preform made by performing injection molding on a synthetic resin material. A material of the bottle 30 to be used is preferably a thermoplastic resin, in particular, polyethylene (PE), polypropylene (PP), polyethylene-terephthalate (PET), or polyethylene naphthalate (PEN). In addition, the container may be glass, a can, paper, a pouch, or a composite container of these. The present embodiment will describe an example of a case where a bottle is used for the container.

As illustrated in FIG. 1, the content filling system 10 includes a bottle feeding portion 21, a sterilizer 11, an air rinse device 14, a sterile water rinse device 15, a filling device (filler) 20, a cap attachment device (a capper, a seamer, and a capping machine) 16, and a product bottle conveyor 22. These bottle feeding portion 21, sterilizer 11, air rinse device 14, sterile water rinse device 15, filling device 20, cap attachment device 16, and product bottle conveyor 22 are disposed in this order along a conveying direction of the bottle 30 from an upstream side to a downstream side. Between the sterilizer 11, the air rinse device 14, the sterile water rinse device 15, the filling device 20, and the cap attachment device 16, a plurality of convey wheels 12 for conveying the bottle 30 between these devices is provided.

The bottle feeding portion 21 successively receives the empty bottle 30 from an outside to the content filling system 10, and conveys the received bottle 30 to the sterilizer 11.

A bottle molding portion (not illustrated) which molds the bottle 30 by performing biaxial stretching blow molding on a preform may be provided on the upstream side of the bottle feeding portion 21. As described above, the process starting upon feeding of the preform, and then molding of the bottle 30, and ending upon filling of the bottle 30 with the content and capping may be performed continuously. In this case, instead of the bottle 30 having a large volume, a preform having a small volume can be carried from the outside to the content filling system 10, so that equipment constituting the content filling system 10 can be reduced in size.

The sterilizer 11 sterilizes the interior of the bottle 30 by injecting a sterilant into the bottle 30. As the sterilant, a hydrogen peroxide aqueous solution is used, for example. In the sterilizer 11, after a hydrogen peroxide aqueous solution having a concentration of 1% by weight or more, preferably 35% by weight is temporarily vaporized, condensed mist or gas is generated, and the mist or gas is sprayed on inner and outer surfaces of the bottle 30. Since the inside of the bottle 30 is thus sterilized by the mist or gas of the hydrogen peroxide aqueous solution, the inner surface of the bottle 30 is sterilized uniformly.

The air rinse device 14 supplies sterile heated air or room temperature air into the bottle 30 to remove foreign matter, hydrogen peroxide, and the like from the inside of the bottle 30 while activating the hydrogen peroxide.

The sterile water rinse device 15 washes the bottle 30, sterilized by hydrogen peroxide as a sterilant, with sterilized water at 15° C. to 85° C. As a result, hydrogen peroxide adhering to the bottle 30 is washed off, and foreign matter is removed.

The filling device 20 fills the previously sterilized content from a mouth of the bottle 30 into the bottle 30. This filling device 20 fills the content in the empty bottle 30. In the filling device 20, while a plurality of the bottles 30 is rotated (revolved), the content is filled inside the bottles 30. This content may be filled inside the bottle 30 at room temperature. The content is sterilized by heating or the like in advance, cooled to room temperature of 3° C. or more and 40° C. or less, and then filled inside the bottle 30. Examples of contents to be filled by the filling device 20 include beverages such as tea-type beverages and milk-type beverages.

The cap attachment device 16 caps the bottle 30 by attaching the cap 33 to the mouth of the bottle 30 filled with the content by the filling device 20. In the cap attachment device 16, the mouth of the bottle 30 is capped with the cap 33 and then sealed so as to prevent external air or virus from invading into the bottle 30. In the cap attachment device 16, while the plurality of bottles 30 filled with the content rotates (revolves), the caps 33 are attached to the mouths of the bottles 30. Thus, by attaching the cap 33 to the mouth of the bottle 30, it is possible to obtain the product bottle 35.

The cap 33 is sterilized by the cap sterilizer 50 in advance. The cap sterilizer 50 is disposed outside a sterile chamber 13 (to be described later) and near the cap attachment device 16, for example. In the cap sterilizer 50, a large number of the caps 33 carried in from the outside are preliminarily collected and then conveyed in a row toward the cap attachment device 16. Mist or gas of hydrogen peroxide is blown against inner and outer surfaces of the cap 33 on the way of conveyance of the cap 33 toward the cap attachment device 16 and then the cap 33 is dried with hot air and sterilized. The configuration of the cap sterilizer 50 thus configured will be described later.

The product bottle conveyor 22 continuously conveys the product bottle 35 with the cap 33 attached by the cap attachment device 16 to the outside of the content filling system 10.

In addition, the content filling system 10 includes the sterile chamber 13. The sterile chamber 13 houses the sterilizer 11, the air rinse device 14, the sterile water rinse device 15, the filling device 20, and the cap attachment device 16, which have been described above. This content filling system 10 may be, for example, a sterile filling system. In this case, the interior of the sterile chamber 13 is kept in a sterile state.

Alternatively, the content filling system 10 may be a high temperature filling system that fills a content at a high temperature of 85° C. or more and less than 100° C. The content filling system 10 may also be a medium temperature filling system that fills a content at a medium temperature of 55° C. or more and less than 85° C.

(Cap Sterilizer)

Figure 2:
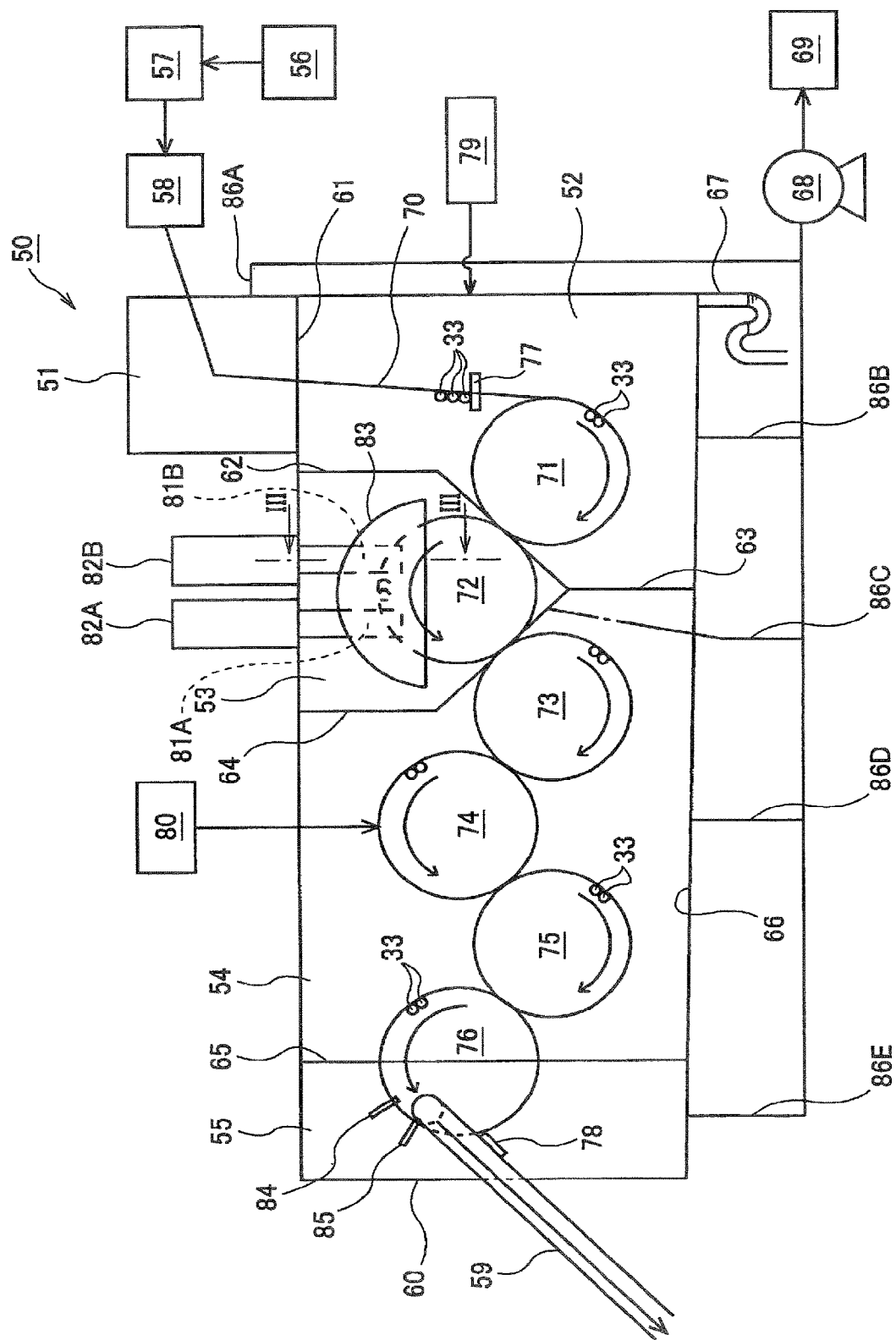
FIG. 2 is a schematic front view illustrating a cap sterilizer according to the first embodiment of the present invention.

Next, the configuration of the cap sterilizer 50 described above will be described with reference to FIG. 2. FIG. 2 is a schematic front view illustrating the cap sterilizer 50 according to the present embodiment. In FIG. 2, a paper surface upward direction indicates upward in a vertical direction, and a paper surface downward direction indicates downward in the vertical direction.

As illustrated in FIG. 2, the cap sterilizer 50 includes a first infeed (introduction) chamber 51, a second infeed (introduction) chamber 52, a sterilant atomizing (disinfectant spray) chamber 53, an air rinse chamber 54, and a washing chamber 55. The first infeed chamber 51, the second infeed chamber 52, the sterilant atomizing chamber 53, the air rinse chamber 54, and the washing chamber 55 are arranged in this order along the conveying direction of the cap 33. The chambers 51, 52, 53, 54, and 55 are arranged inside a housing 60.

The first infeed chamber 51 and the second infeed chamber 52 are separated by a partition wall 61 provided therebetween. Likewise, the second infeed chamber 52 and the sterilant atomizing chamber 53 are separated by a partition wall 62, the second infeed chamber 52 and the air rinse chamber 54 are separated by a partition wall 63, and the sterilant atomizing chamber 53 and the air rinse chamber 54 are separated by a partition wall 64. In addition, the air rinse chamber 54 and the washing chamber 55 are separated by a partition wall 65.

The partition walls 61, 62, 63, 64, and 65 prevent gas, water, and the like from flowing between the chambers 51, 52, 53, 54, and 55 and play a role of stabilizing the pressures in the chambers 51, 52, 53, 54, and 55. However, gaps are formed in the respective partition walls 61, 62, 63, 64, and 65 so that the cap 33 or the like can pass therethrough. The size of each gap is decreased to the minimum, for example, a comparable size to the cap 33, so that the pressures in the chambers 51, 52, 53, 54, and 55 do not change.

A hopper 56, a sorter 57, and a cap inspection machine 58 are provided on the previous process side of the first infeed chamber 51 and outside the housing 60. A large number of the caps 33 are randomly charged into the hopper 56 from the outside. The sorter 57 arranges the caps 33, randomly charged into the hopper 56, in one row or multiple rows and conveys the caps 33 from a lower side to an upper side in the vertical direction. The cap inspection machine 58 inspects the shape and the like of each of the caps 33 and discharges the caps 33 failed in inspection. The caps 33 which have passed the inspection are conveyed in a row toward the first infeed chamber 51.

The cap 33 is a well-known one and has a substantially circular planar shape with an opening on the inner surface side. As the cap 33, one formed of a thermoplastic resin such as high density polyethylene (HDPE), polypropylene (PP), and biodegradable plastic can be used. As the cap 33, in addition to a normal bottle cap, a composite cap or a sport cap may be used.

In the first infeed chamber 51 and the second infeed chamber 52, a conveyance guide 70 for conveying a plurality of the caps 33 in a row is provided. The conveyance guide 70 may include, for example, a plurality of rails. In this case, a space is formed in a region surrounded by the plurality of rails so that the cap 33 does not come off, and the cap 33 is accommodated in this space and conveyed. The cap 33 is transferred from the first infeed chamber 51 side toward the second infeed chamber 52 by its own weight. By providing the conveyance guide 70 thus configured, it is possible to convey the cap 33 at high speed from the first infeed chamber 51 to the second infeed chamber 52.

The second infeed chamber 52, the sterilant atomizing chamber 53, the air rinse chamber 54, and the washing chamber 55 include respectively rotation conveyance mechanisms 71 to 76 for rotating and conveying the caps 33. Among them, the first rotation conveyance mechanism 71 is provided in the second infeed chamber 52, and the second rotation conveyance mechanism 72 is provided in the sterilant atomizing chamber 53. The air rinse chamber 54 and the washing chamber 55 include a total of four rotation conveyance mechanisms 73 to 76 (a third rotation conveyance mechanism 73, a fourth rotation conveyance mechanism 74, a fifth rotation conveyance mechanism 75, a sixth rotation conveyance mechanism 76). Among them, the three rotation conveyance mechanisms 73 to 75 are arranged inside the air rinse chamber 54, and the sixth rotation conveyance mechanism 76 is disposed to straddle the air rinse chamber 54 and the washing chamber 55. The rotation conveyance mechanisms 71 to 76 each rotate (on their axes) along axes parallel to the horizontal direction, thereby rotating (revolving) and conveying a plurality of the caps 33. The rotation conveyance mechanisms 71 to 76 each have a star wheel located at the center and provided with a notch for accommodating the cap 33 and a plurality of rails arranged around the star wheel and preventing the cap 33 from coming off. The cap 33 is conveyed as the star wheel is driven, guided by the rail, accommodated, and rotated (revolved). By using the rotation conveyance mechanisms 71 to 76 thus configured, it is possible to convey the cap 33 at high speed within the cap sterilizer 50.

A drainage pipe 67 is formed on a bottom surface 66 of the housing 60 and inside the second infeed chamber 52. The bottom surface 66 is inclined downward from the washing chamber 55 toward the second infeed chamber 52. Due to this, droplets generated inside the housing 60 due to condensation or the like can be discharged to the outside of the housing 60 through the drainage pipe 67. The drainage pipe 67 is curved partway in an S shape, and a drainage remains in the S-shaped portion, whereby an internal pressure of the second infeed chamber 52 is maintained (water sealing mechanism).

Next, the configuration of each of the chambers 51, 52, 53, 54, and 55 will be further described.

The cap 33 from the cap inspection machine 58 is introduced into the first infeed chamber 51, and the first infeed chamber 51 is disposed above the second infeed chamber 52. The interior of the first infeed chamber 51 is maintained at a negative pressure or a slight positive pressure (for example, −100 Pa or more and 10 Pa or less), so that a steam containing a sterilant is prevented from leaking to the outside of the housing 60. The first infeed chamber 51 is provided mainly to prevent the steam containing the sterilant from leaking to the outside, so that the volume of the first infeed chamber 51 may be smaller than the volume of the second infeed chamber 52. Unlike the second infeed chamber 52, the first infeed chamber 51 is not provided with a rotation conveyance mechanism for rotating and conveying the cap 33.

The cap 33 is fed from the first infeed chamber 51 to the second infeed chamber (infeed chamber) 52 by the conveyance guide 70. Sterile hot air from a first hot air supplier 79 is sent into the second infeed chamber 52. The temperature of sterile hot air is, for example, 40° C. or more and 120° C. or less. Thus, the interior of the second infeed chamber 52 is maintained at a temperature of, for example, 30° C. or more and 80° C. or less. This suppresses condensation of the sterilant inside the second infeed chamber 52 and can prevent variation in the extent of sterilization among the plurality of caps 33 due to the fact that a liquid sterilant remains in the cap 33. The interior of the second infeed chamber 52 is maintained at a positive pressure (for example, 0 Pa or more and 200 Pa or less), so that the sterilant is prevented from excessively flowing into the second infeed chamber 52. Inside the second infeed chamber 52, the conveyance guide 70 is provided with a first stopper 77 which is freely opened and closed. When the first stopper 77 is opened, the cap 33 is sent to the first rotation conveyance mechanism 71, and when the first stopper 77 is closed, the cap 33 stays at this position. The first hot air supplier 79 may be disposed on a conveyance path of the first rotation conveyance mechanism 71, and the temperature of the cap 33 may be preliminarily increased by hot air from the first hot air supplier 79.

The sterilant atomizing chamber 53 sprays a sterilant against the cap 33 fed from the second infeed chamber 52 by the first rotation conveyance mechanism 71. The sterilant atomizing chamber 53 is disposed above the second infeed chamber 52. Depending on the positional relationship of the first rotation conveyance mechanism 71 and the like, the second infeed chamber 52 may be located above the sterilant atomizing chamber 53. Here, the sterilant is, for example, hydrogen peroxide solution. The cap 33 sent from the first rotation conveyance mechanism 71 is delivered to the second rotation conveyance mechanism 72, and while the cap 33 is conveyed by the second rotation conveyance mechanism 72, the sterilant is sprayed by spray nozzles 81A and 81B. At the top of the sterilant atomizing chamber 53, two sterilant spray devices 82A and 82B are arranged. Among the sterilant spray devices, the sterilant spray device 82A is connected to the spray nozzle 81A for outer surface which supplies the sterilant to the outer surface (top surface portion) side of the cap 33. On the other hand, the other sterilant spray device 82B is connected to the spray nozzle 81B for inner surface which supplies the sterilant to the inner surface (opening) side of the cap 33.

It is preferable that the spray nozzle 81A for outer surface is located downstream of the spray nozzle 81B for inner surface in the conveying direction of the cap 33 (the spray nozzle 81A may be located upstream of the spray nozzle 81B in the conveying direction of the cap 33). That is, it is preferable to first supply the sterilant to the inner surface of the cap 33 by the spray nozzle 81B on the conveyance path of the second rotation conveyance mechanism 72, and then supply the sterilant to the outer surface of the cap 33 by the spray nozzle 81A. Thus, it is possible to sterilize the inner surface of the cap 33, which needs to be more reliably sterilized, prior to the outer surface of the cap 33. In order to adhere the sterilant to every corner of a complicated shape of the inner surface of the cap 33 conveyed at high speed, the spray nozzles 81A and 81B have an inner diameter of $\varphi$ 2 mm or more and $\varphi$ 15 mm or less (preferably $\varphi$ 3 mm or more and $\varphi$ 10 mm or less) and preferably have an outer diameter of 2 mm or more (preferably 4 mm or more) thicker than the inner diameter so as to prevent reduction in temperature of hydrogen peroxide gas and occurrence of liquid sagging. If the nozzle inner diameter is less than $\varphi$ 2 mm, a stabilizer of hydrogen peroxide accumulates during long-term use, which may clog the nozzle. A distance between the cap 33 and the tips of the spray nozzles 81A and 81B is preferably 5 mm or more and 100 mm or less.

A cover 83 having a fan or arc-shape as viewed from the front side, for example, is disposed at an upper portion of the second rotation conveyance mechanism 72 and around the spray nozzles 81A and 81B. The cover 83 covers the surroundings of the spray nozzles 81A and 81B, prevents the sterilant from the spray nozzles 81A and 81B from scattering to the surroundings, and enables effective spraying of the sterilant to the cap 33. The interior of the sterilant atomizing chamber 53 is maintained at a positive pressure (for example, 0 Pa or more and 50 Pa or less), whereby the sterilant is prevented from excessively flowing out of the sterilant atomizing chamber 53. An adhesion amount of hydrogen peroxide necessary for sterilizing the cap 33 is 0.6 $\mu L/cm^2$ or more and 4.7 $\mu L/cm^2$ or less (preferably 1.2 $\mu L/cm^2$ or more and 2.4 $\mu L/cm^2$ or less) in terms of 35% by weight. Within this range, the cap 33 can be sterilized at high speed, and a medicine can be reliably removed by air rinsing to be described later.

Figure 3:
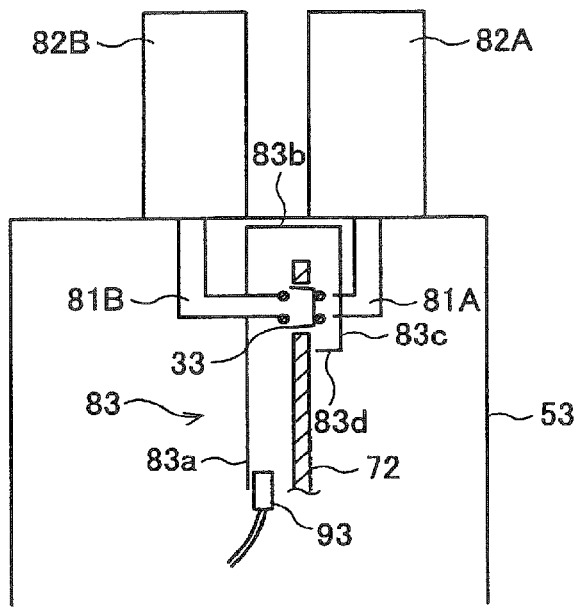
FIG. 3 is a schematic cross-sectional view (cross-sectional view taken along the line III-III in FIG. 2) illustrating a sterilant atomizing chamber of the cap sterilizer according to the first embodiment of the present invention.

FIG. 3 illustrates a vertical cross section of the interior of the sterilant atomizing chamber 53. As illustrated in FIG. 3, the cover 83 is disposed inside the sterilant atomizing chamber 53. The cover 83 has a front plate 83a, a top plate 83b, a rear plate 83c, and a bottom plate 83d which are connected to each other. Among them, the front plate 83a has a fan or arc-shape when viewed from the front side and is larger than the rear plate 83c. The front plate 83a may have a transparent confirmation window so that the interior of the cover 83 can be visually observed. The spray nozzle 81B for inner surface extends from the front plate 83a toward the interior of the cover 83, and the spray nozzle 81A for outer surface extends from the rear plate 83c toward the interior of the cover 83. In FIG. 3, the spray nozzle 81B is located on the front side (the upstream side in the conveying direction of the cap 33) with respect to the spray nozzle 81A. As described above, in the space surrounded by the cover 83, the sterilant is sprayed against the cap 33 from the spray nozzles 81A and 81B. At this time, since the concentration of the sterilant inside the cover 83 can be increased, the cap 33 can be effectively sterilized. Since the tips of the spray nozzles 81A and 81B are covered with the cover 83, the amount of the sterilant leaking to the outside of the cover 83 is reduced, whereby the amount of the sterilant leaking to the outside of the sterilant atomizing chamber 53 can also be reduced.

A washing nozzle 93 which ejects a washing liquid toward the interior of the cover 83 is provided inside the cover 83. In this case, the washing nozzle 93 is disposed so as to face upward between the front plate 83a and the second rotation conveyance mechanism 72. Examples of the washing liquid ejected from the washing nozzle 93 include a single preparation or a mixed preparation containing components such as water, an alkaline solution, alcohol, chlorine, peracetic acid, and hydrogen peroxide and sterile water used to wash away a medicine after washing/sterilization. As described above, by ejecting the washing liquid from the washing nozzle 93, it is possible to wash equipment in the cover 83 before sterilizing the cap 33. For example, an inner wall surface of the cover 83, the spray nozzles 81A and 81B, the second rotation conveyance mechanism 72, and the like can be washed. Consequently, it is possible to effectively perform, for example, Cleaning out of Place (COP) treatment or Sterilizing out of Place (SOP) treatment on the sterilant atomizing chamber 53.

Figure 4:
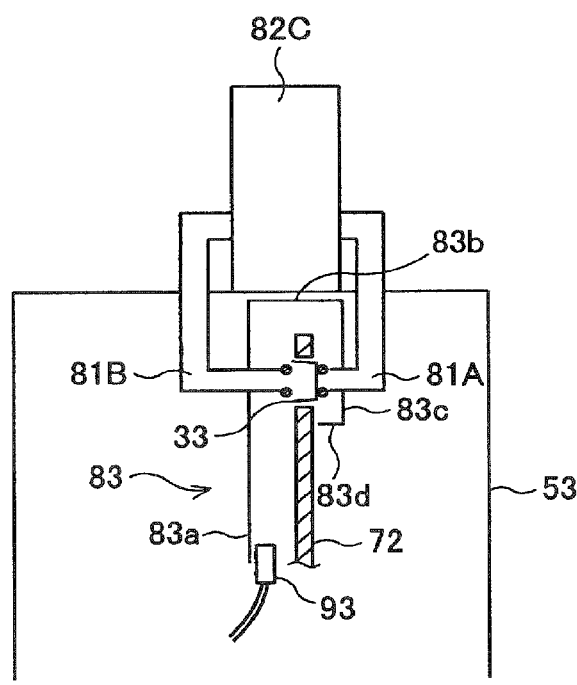
FIG. 4 is a schematic cross-sectional view illustrating a modification of the sterilant atomizing chamber.

FIG. 4 illustrates a modification of the sterilant atomizing chamber 53. As illustrated in FIG. 4, the spray nozzles 81A and 81B are arranged at substantially the same position when viewed from the front side (left side in FIG. 4). In this case, the spray nozzles 81A and 81B spray the sterilant against the inner and outer surfaces of the cap 33 at substantially the same timing. A sterilant spray device 82C is provided above the sterilant atomizing chamber 53, and a sterilant is supplied to both of the spray nozzles 81A and 81B from the sterilant spray device 82C. In this case, since the positions of the spray nozzles 81A and 81B can be made substantially the same in the conveying direction of the cap 33, the sterilant atomizing chamber 53 can be compactly configured.

Figure 5:
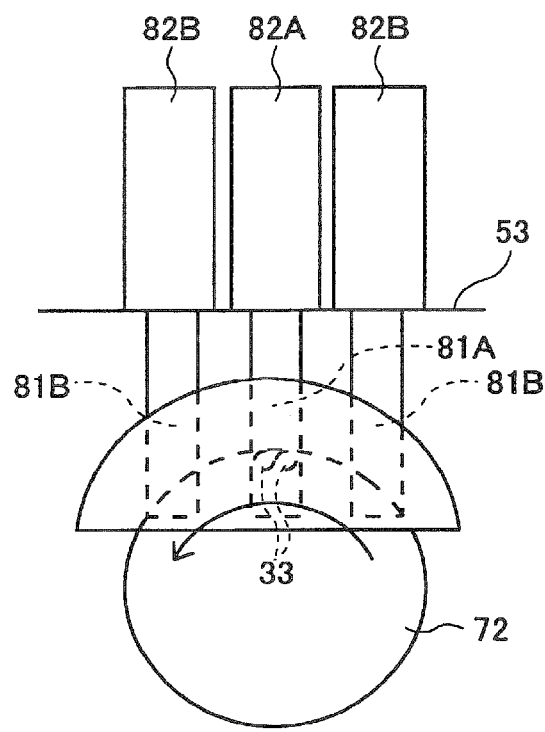
FIG. 5 is a schematic front view illustrating a modification of the sterilant atomizing chamber.

FIG. 5 illustrates another modification of the sterilant atomizing chamber 53. In FIG. 5, the three spray nozzles 81B, 81A, and 81B spray the sterilant against the cap 33. That is, the spray nozzle 81B for inner surface, the spray nozzle 81A for outer surface, and the spray nozzle 81B for inner surface are arranged in this order from the upstream side in the conveying direction of the cap 33 to the downstream side. Thus, it is possible to spray a relatively large amount of the sterilant against the inner surface of the cap 33 which needs to be more reliably sterilized. In this case, it is possible to increase the conveying speed of the cap 33, for example, to about 800 cpm or more and 1500 cpm or less.

As the sterilant, besides hydrogen peroxide, alcohols such as peracetic acid, nitric acid, chlorine sterilant, sodium hydroxide, potassium hydroxide, ethyl alcohol, and isopropyl alcohol, chlorine dioxide, ozone water, acid water, and surfactant may be used alone, or two or more of these may be used in combination at any ratio.

Referring again to FIG. 2, the air rinse chamber 54 air-rinses the cap 33 sprayed with the sterilant in the sterilant atomizing chamber 53. The cap 33 is sequentially conveyed by the rotation conveyance mechanisms 73 to 76 in the air rinse chamber 54, and meanwhile, sterile hot air is blown against both the inner and outer surfaces of the cap 33. Sterile hot air from a second hot air supplier 80 is sent into the air rinse chamber 54. In this case, sterile hot air is blown against the cap 33 passing through the fourth rotation conveyance mechanism 74. Sterile hot air may be blown against the cap 33 passing through the fifth rotation conveyance mechanism 75 and/or the sixth rotation conveyance mechanism 76. The temperature of sterile hot air is, for example, 80° C. or more and 140° C. or less, preferably 90° C. or more and 120° C. or less. The air volume of sterile hot air is, for example, 5 m$^3$/min or more and 20 m$^3$/min or less. The sterile hot air blowing time is 1 second or more and 20 seconds or less, preferably 3 seconds or more and 14 seconds or less. By blowing sterile hot air against the cap 33, the temperature of the cap 33 is raised to 40° C. or more, preferably 50° C. or more. As a result, the sterilant adhering to the cap 33 is removed. The interior of the air rinse chamber 54 is maintained at a positive pressure (for example, 30 Pa or more and 200 Pa or less, preferably 50 Pa or more and 150 Pa or less). Sterile hot air may contain a trace amount of a component of a sterilant such as hydrogen peroxide.

Figure 6:
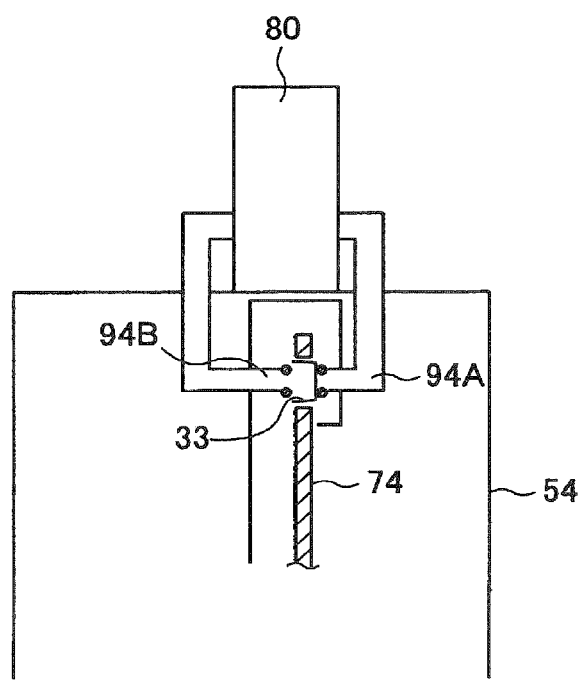
FIG. 6 is a partial schematic cross-sectional view illustrating an air rinse chamber.

FIG. 6 illustrates a vertical cross section of the interior of the air rinse chamber 54. As illustrated in FIG. 6, air rinse nozzles 94A and 94B are arranged inside the air rinse chamber 54. The air rinse nozzles 94A and 94B are connected to the second hot air supplier 80 and each blow out sterile hot air supplied from the second hot air supplier 80. Among the air rinse nozzles, the air rinse nozzle 94A blows sterile hot air against the outer surface of the cap 33, and the air rinse nozzle 94B blows sterile hot air against the inner surface of the cap 33. The air rinse nozzles 94A and 94B are arranged at substantially the same position when viewed from the front side (left side in FIG. 6). In this case, the air rinse nozzles 94A and 94B spray sterile hot air against the inner and outer surfaces of the cap 33 at substantially the same timing. As described above, in the space surrounded by the air rinse chamber 54, sterile hot air is blown against both the inner and outer surfaces of the cap 33 from the air rinse nozzles 94A and 94B. Thus, it is possible to reliably remove the sterilant adhering to the inner surface and the outer surface of the cap 33 in the sterilant atomizing chamber 53.

Referring to FIG. 2, the washing chamber 55 washes the cap 33 which has been air-rinsed in the air rinse chamber 54. The cap 33 is conveyed by the sixth rotation conveyance mechanism 76 in the washing chamber 55. Meanwhile, first, a washing liquid such as sterile water is blown against the inner and outer surfaces of the cap 33 by the washing nozzle 84. As a result, even when foreign matter is adhering to the cap 33, it is possible to reliably remove the foreign matter and to cool the cap 33 heated with sterile hot air. Then, sterile air is blown against the inner and outer surfaces of the cap 33 by the air blow nozzle 85, and the washing liquid such as sterile water adhering to the cap 33 is removed. Even after the sterile air is blown, sterile water slightly remains in the cap 33. This makes it possible to improve lubrication between the cap 33 and a chute 59 to be described later while the cap 33 is conveyed by the chute 59 and to prevent the temperature of the cap 33 from rising due to frictional heat with the chute 59. By suppressing the rise in the temperature of the cap 33 as described above, it is possible to stably perform seaming operation of the cap 33 in the cap attachment device 16. The interior of the washing chamber 55 is maintained at a positive pressure (for example, Pa or more and 200 Pa or less). This prevents an atmosphere containing a sterilant from flowing out toward the cap attachment device 16. In the present embodiment, the washing chamber 55 is not necessarily provided. When a lubricant adheres to the cap 33, such as when a carbonic acid cap is used as the cap 33, the washing nozzle 84 may be temporarily stopped so that the lubricant does not peel off.

The chute 59 for conveying the cap 33 toward the cap attachment device 16 is connected to the washing chamber 55. The chute 59 may include, for example, a plurality of rails. In this case, a space is formed in a region surrounded by the plurality of rails so that the cap 33 does not come off, and the cap 33 is accommodated in this space and conveyed. In the washing chamber 55, the chute 59 is provided with an openable and closable second stopper 78. When the second stopper 78 is opened, the cap 33 is sent to the cap attachment device 16 by the chute 59. On the other hand, when the second stopper 78 is closed, the cap 33 stays at this position. Alternatively, the second stopper 78 may be provided on the chute 59 and near the cap attachment device 16.

In the present embodiment, exhaust pipes 86A to 86E are connected respectively to the first infeed chamber 51, the second infeed chamber 52, the sterilant atomizing chamber 53, the air rinse chamber 54, and the washing chamber 55. The first infeed chamber 51, the second infeed chamber 52, the sterilant atomizing chamber 53, the air rinse chamber 54, and the washing chamber 55 are exhausted via the respective exhaust pipes 86A to 86E. A blower 68 which draws gas in the exhaust pipes 86A to 86E is connected to the exhaust pipes 86A to 86E, and a scrubber 69 which processes components of a sterilant of the gas is connected to the blower 68.

In this case, the exhaust pressure E4 in the air rinse chamber 54 is higher than the exhaust pressure E1 in the first infeed chamber 51. As a result, even if a large air volume of sterile hot air is supplied to the air rinse chamber 54, air is sucked from the air rinse chamber 54, and it is possible to prevent the pressure in the air rinse chamber 54 from excessively increasing.

The exhaust pressure E5 in the washing chamber 55 is higher than the exhaust pressure E1 in the first infeed chamber 51. This makes it possible to strongly suck a gas containing a sterilant from the washing chamber 55 and to prevent the atmosphere containing the sterilant from flowing out toward the cap attachment device 16.

The exhaust pressure E1 in the first infeed chamber 51 is higher than the exhaust pressure E2 in the second infeed chamber 52. This makes it possible to strongly suck a gas containing a sterilant from the first infeed chamber 51 and to prevent the atmosphere containing the sterilant from flowing out of the housing 60.

The exhaust pressure E2 in the second infeed chamber 52 is higher than the exhaust pressure E3 in the sterilant atomizing chamber 53. That is, the exhaust pressure E3 in the sterilant atomizing chamber 53 is lower than any of the exhaust pressures E1, E2, E4, and E5 of the other chambers 51, 52, 54, and 55. The sterilant atomizing chamber 53 is not necessarily exhausted (the exhaust pressure may be 0). As a result, the gas containing the sterilant stays in the second infeed chamber 52, and it is possible to prevent the gas containing the sterilant from condensing in the second infeed chamber 52. On the other hand, the exhaust pressure E3 in the sterilant atomizing chamber 53 is sufficiently weakened, or the interior of the sterilant atomizing chamber 53 is not exhausted, whereby the concentration of the sterilant is increased in the atmosphere of the sterilant atomizing chamber 53, and the cap 33 can be reliably sterilized in the sterilant atomizing chamber 53. By increasing the concentration of the sterilant in the sterilant atomizing chamber 53, even when the cap 33 is conveyed at high speed, the cap 33 can be sterilized reliably.

In summary, a relationship E5, E4>E1>E2>E3 holds. The relationship between E5 and E4 does not matter. If the positive pressure of the cap sterilizer 50 is higher than the positive pressure of a capper portion of a filling chamber of the filling device 20, the cap 33 can be conveyed well. Specifically, it is better to increase the positive pressure of the cap sterilizer 50 higher by 30 Pa or more and 200 Pa or less than the positive pressure of the filling chamber. When a differential pressure of 200 Pa or more is provided, sterilant gas (hydrogen peroxide) from the cap sterilizer 50 flows into the filling chamber, and there is a risk that the sterilant will dissolve in a product liquid at a filling valve opening.

Throughout the cap sterilizer 50, the conveying speed of the cap 33 is 100 cpm or more and 1500 cpm or less, preferably 500 cpm or more and 1000 cpm or less. According to the cap sterilizer 50 according to the present embodiment, even when the cap 33 is conveyed at high speed as described above, the cap 33 can be sterilized reliably. The number of the caps 33 passing through a predetermined position per minute is represented by cap per minute (cpm). When the filling speed of the bottle 30 is slow, such as when the bottle 30 is a large size bottle (having an inner capacity of 1 L or more), the conveying speed of the cap 33 may be made slower than the above speed in accordance with this filling speed. In this case, supply conditions (temperature, flow rate, etc.) of hot air in the second infeed chamber 52 and the air rinse chamber 54 may be adjusted so that the temperature of the cap 33 does not rise.

In the present embodiment, the case in which the two chambers, the first infeed chamber 51 and the second infeed chamber 52, are provided as infeed chambers has been described as an example, but the present invention is not limited to this example. A single infeed chamber may be provided by combining the first infeed chamber 51 and the second infeed chamber 52. Further, in the present embodiment, the case in which rotary shafts of the rotation conveyance mechanisms 71 to 76 are oriented in the horizontal direction so that the cap 33 is conveyed in a substantially vertical plane has been described as an example. However, the present invention is not limited to this example, and the rotary shafts of the rotation conveyance mechanisms 71 to 76 may be oriented in the vertical direction so that the cap 33 is conveyed in a substantially horizontal plane.

(Content Filling Method)

Next, a content filling method using the above-described content filling system 10 (FIG. 1) will be described. In the following description, a filling method at a normal time, that is, a content filling method in which a content such as a beverage is filled inside the bottle 30 to produce the product bottle 35 will be described.

First, the plurality of empty bottles 30 is sequentially fed from the outside of the content filling system 10 to the bottle feeding portion 21. The bottle 30 is sent from the bottle feeding portion 21 to the sterilizer 11 by the convey wheel 12 (container feeding step).

Then, in the sterilizer 11, the bottle 30 is sterilized using a hydrogen peroxide aqueous solution as a sterilant (bottle sterilization step). At this time, the hydrogen peroxide aqueous solution is a gas or mist condensed after a hydrogen peroxide aqueous solution having a concentration of 1% by weight or more, preferably 35% by weight is temporarily vaporized, and the mist or gas is supplied toward the bottle 30.

Subsequently, the bottle 30 is sent to the air rinse device 14 by the convey wheel 12, and sterile heated air or room temperature air is supplied in the air rinse device 14, whereby foreign matter, hydrogen peroxide, and the like are removed from the bottle 30 while hydrogen peroxide is activated. Subsequently, the bottle 30 is conveyed to the sterile water rinse device 15 by the convey wheel 12. In the sterile water rinse device 15, washing with sterile water at 15° C. to 85° C. is performed (rinsing step). Specifically, sterile water at 15° C. to 85° C. is supplied into the bottle 30 at a flow rate of 5 L/min or more and 15 L/min or less. At this time, preferably, the bottle 30 takes an inverted attitude, and the sterile water is supplied into the bottle 30 through the downwardly opened mouth, and flows out of the bottle 30 from the mouth. With this sterile water, hydrogen peroxide adhering to the bottle 30 is washed off, and foreign matter is removed. The step of supplying sterile water into the bottle 30 is not necessarily provided.

Subsequently, the bottle 30 is conveyed to the filling device 20 by the convey wheel 12. In the filling device 20, while the bottle 30 is rotated (revolved), the content is filled inside the bottle 30 from the mouth (filling step). In the filling device 20, the contents are prepared in advance, and the content heated and sterilized and then cooled to the room temperature is filled inside the sterilized bottle 30 at the room temperature.

Subsequently, the bottle 30 filled with the content is conveyed to the cap attachment device 16 by the convey wheel 12.

On the other hand, the cap 33 is sterilized by the cap sterilizer 50 illustrated in FIG. 2 in advance (cap sterilization step). Meanwhile, first, a large number of the caps 33 are randomly charged into the hopper 56 from the outside of the cap sterilizer 50. Then, the caps 33 randomly charged into the hopper 56 are aligned by the sorter 57 and then conveyed to the cap inspection machine 58. Then, in the cap inspection machine 58, the shape and the like of each of the caps 33 are inspected, and the caps 33 which have passed the inspection are conveyed in a row toward the first infeed chamber 51.

The cap 33 introduced into the first infeed chamber 51 is sent to the second infeed chamber 52 by the conveyance guide 70. As described above, the interior of the second infeed chamber 52 is maintained at, for example, 30° C. or more and 80° C. or less by sterile hot air. Then, the cap 33 is conveyed in the second infeed chamber 52 by the first rotation conveyance mechanism 71 and sent to the sterilant atomizing chamber 53. Subsequently, in the sterilant atomizing chamber 53, while the cap 33 is conveyed by the second rotation conveyance mechanism 72, a sterilant such as a hydrogen peroxide solution is sprayed from the spray nozzles 81A and 81B, and the inner and outer surfaces of the cap 33 are sterilized.

Subsequently, the cap 33 sprayed with the sterilant is sent to the air rinse chamber 54.

In the air rinse chamber 54, the cap 33 is sequentially conveyed by the rotation conveyance mechanisms 73 to 76 in the air rinse chamber 54, and meanwhile, sterile hot air is blown against the inner and outer surfaces of the cap 33. As a result, the sterilant adhering to the cap 33 is air-rinsed.

Then, the cap 33 is sent from the air rinse chamber 54 to the washing chamber 55. In the washing chamber 55, while the cap 33 is conveyed by the sixth rotation conveyance mechanism 76, a washing liquid such as sterile water is blown against the cap 33 by the washing nozzle 84, and foreign matter and the like adhering thereto are removed and cooled. Subsequently, sterile air is blown against the cap 33 by the air blow nozzle 85, and sterile water is removed. At this time, sterile water adhering to the cap 33 is not completely removed, but a part of sterile water is left. This makes it possible to prevent the temperature of the cap 33 from rising due to frictional heat with the chute 59 and to stably perform seaming operation of the cap 33 in the cap attachment device 16. Since a trace amount of sterile water remains, the sterile water is removed by, for example, the frictional heat described above by the time the cap 33 reaches the cap attachment device 16.

Thereafter, the cap 33 is carried from the washing chamber 55 and sent to the cap attachment device 16 by the chute 59.

Referring again to FIG. 1, the cap 33 sterilized by the cap sterilizer 50 as described above is attached to the mouth of the bottle 30 which has been conveyed from the filling device 20 in the cap attachment device 16. Consequently, the product bottle 35 having the bottle 30 and the cap 33 is obtained (cap attaching step).

Thereafter, the product bottle 35 is conveyed from the cap attachment device 16 to the product bottle conveyor 22 and is carried toward the outside of the content filling system 10.

The respective steps from the sterilization step to the cap attachment step are performed in a sterile atmosphere surrounded by the sterile chamber 13, that is, in a sterile environment. After the sterilization treatment, aseptic air of positive pressure is supplied into the sterile chamber 13 so that the aseptic air is always blown toward the exterior of the sterile chamber 13.

The production (conveying) speed of the bottle 30 in the content filling system 10 is preferably 100 bpm or more and 1500 bpm or less. Here, the conveying speed of the bottle 30 per minute is represented by bottle per minute (bpm).

As described above, according to the present embodiment, the cap sterilizer 50 is divided into the plurality of chambers 51, 52, 53, 54, and 55, and the pressure in each of the chambers 51, 52, 53, 54, and 55 is controlled. Thus, while the cap 33 is conveyed at high speed in the cap sterilizer 50, the cap 33 can be reliably sterilized.

Specifically, the exhaust pressure E4 in the air rinse chamber 54 is higher than the exhaust pressure E1 in the first infeed chamber 51. As a result, even if a large air volume of sterile hot air is supplied to the air rinse chamber 54 in order to reliably air-rinse the cap 33 conveyed at high speed, sterile hot air can be removed from the air rinse chamber 54 without being left.

The exhaust pressure E1 in the first infeed chamber 51 is higher than the exhaust pressure E2 in the second infeed chamber 52. As a result, even if the concentration of the sterilant in the sterilant atomizing chamber 53 is increased in order to reliably sterilize the cap 33 conveyed at high speed, it is possible to prevent the atmosphere containing the sterilant from flowing out of the housing 60.

Both the exhaust pressure E2 in the second infeed chamber 52 and the exhaust pressure E4 in the air rinse chamber 54 are higher than the exhaust pressure E3 in the sterilant atomizing chamber 53, or the sterilant atomizing chamber 53 is not exhausted. As a result, the concentration of the sterilant can be increased in the sterilant atomizing chamber 53, and the cap 33 conveyed at high speed can be sterilized reliably.

Further, according to the present embodiment, the exhaust pressure E5 in the washing chamber 55 is higher than the exhaust pressure E1 in the first infeed chamber 51. This makes it possible to prevent the atmosphere containing the sterilant from flowing out toward the cap attachment device 16 from the washing chamber 55.

Furthermore, according to the present embodiment, by exhausting the chambers 51, 52, 53, 54, and 55, it is possible to prevent the internal pressure of each of the chambers 51, 52, 53, 54, and 55 from becoming too high. As a result, the cap 33 can be reliably introduced into each of the chambers 51, 52, 53, 54, and 55. On the other hand, if the chambers 51, 52, 53, 54, and 55 are not sufficiently exhausted, the internal pressure of each of the chambers 51, 52, 53, 54, and 55 becomes too high, so that the cap 33 may be unable to enter 51, 52, 53, 54, and 55.

Further, according to the present embodiment, the first infeed chamber 51 into which the cap 33 is introduced, the second infeed chamber 52 into which sterile hot air is sent, and the sterilant atomizing chamber 53 which sprays the sterilant against the cap 33 are arranged in this order along the conveying direction of the cap 33. The first infeed chamber 51 and the second infeed chamber 52 are separated from each other by the partition wall 61. As a result, even when the concentration of the sterilant in the sterilant atomizing chamber 53 is increased, steam containing the sterilant from the sterilant atomizing chamber 53 is prevented from leaking to the outside of the cap sterilizer 50. Accordingly, since the concentration of the sterilant in the sterilant atomizing chamber 53 can be increased, even when the conveying speed of the cap 33 is increased, the cap 33 can be sterilized reliably.

Further, according to the present embodiment, the air rinse chamber 54 which air-rinses the cap 33 sprayed with the sterilant in the sterilant atomizing chamber 53 is provided. This makes it possible to reliably remove the sterilant adhering to the cap 33 in the sterilant atomizing chamber 53.

Further, according to the present embodiment, since the internal pressure of the first infeed chamber 51 is maintained at −100 Pa or more and 10 Pa or less (negative pressure to slight positive pressure), it is possible to prevent steam containing the sterilant agent from leaking from the first infeed chamber 51 to the outside of the cap sterilizer 50. On the other hand, since the internal pressure of the second infeed chamber 52 is maintained at 50 Pa or more and 200 Pa or less (positive pressure), the amount of the sterilant flowing into the second infeed chamber 52 from the sterilant atomizing chamber 53 can be suppressed, and it is possible to more reliably reduce the amount of the sterilant leaking from the second infeed chamber 52 to the outside of the cap sterilizer 50 via the first infeed chamber 51.

Further, according to the present embodiment, the cover 83 covering the surroundings of the spray nozzles 81A and 81B is provided in the sterilant atomizing chamber 53. As a result, the concentration of the sterilant inside the cover 83 can be increased, and the cap 33 can be effectively sterilized. As a result, even when the conveying speed of the cap 33 increases, the cap 33 can be reliably sterilized. Further, even when the concentration of the sterilant in the cover 83 is increased, it is possible to prevent steam containing the sterilant from leaking from the sterilant atomizing chamber 53 to the outside of the cap sterilizer 50.

According to the present embodiment, the cover 83 has a fan or arc-shape when viewed from the front side. That is, the shape of the cover 83 corresponds to the shape of the second rotation conveyance mechanism 72. This makes it possible to reduce the volume of a wasted space in the cover 83 and to efficiently increase the concentration of the sterilant inside the cover 83.

Further, according to the present embodiment, the spray nozzle 81A for outer surface is located downstream of the spray nozzle 81B for inner surface in the conveying direction of the cap 33. Thus, it is possible to lengthen the time during which the sterilant adheres to the inner surface of the cap 33 which needs to be more reliably sterilized and to sterilize the inner surface of the cap 33 more effectively. The spray nozzle 81A may be located upstream of the spray nozzle 81B in the conveying direction of the cap 33.

Furthermore, according to the present embodiment, since the washing nozzle 93 which ejects a washing liquid toward the interior of the cover 83 is provided inside the cover 83, before the cap 33 is sterilized, equipment inside the cover 83 can be washed.

Further, according to the present embodiment, in the air rinse chamber 54, sterile hot air is blown against both the inner and outer surfaces of the cap 33 by the air rinse nozzles 94A and 94B. Thus, in the sterilant atomizing chamber 53, the sterilant adhering to the inner and outer surfaces of the cap 33 can be reliably removed by the spray nozzles 81A and 81B. Accordingly, the high concentration of the sterilant can be blown against the cap 33 by the spray nozzles 81A and 81B, and as a result, the conveying speed of the cap 33 can be increased.

Particularly, as sterile hot air is blown by the air rinse nozzles 94A and 94B, the temperature of the cap 33 rises to 40° C. or more, so that the sterilant on the cap 33 can be reliably removed.

Furthermore, by providing the washing nozzle 84 which washes the cap 33 air-rinsed by the air rinse nozzles 94A and 94B, even when foreign matter adheres to the cap 33, it is possible to reliably remove the foreign matter and to cool the cap 33 heated with sterile hot air.

Further, according to the present embodiment, in the washing chamber 55, a washing liquid such as sterile water is blown against the cap 33 from the washing nozzle 84, whereby the cap 33 is cleaned. This makes it possible to reliably remove foreign matter adhering to the cap 33. In addition, since the cap 33 heated with sterile hot air can be cooled, even when the cap 33 is conveyed at high speed, it is possible to prevent the temperature of the cap 33 from rising due to frictional heat with the chute 59. As a result, it is possible to increase the conveying speed of the cap 33.

Further, according to the present embodiment, in the washing chamber 55, sterile air is blown against the cap 33 by the air blow nozzle 85, whereby a washing liquid adhering to the cap 33 is removed. As a result, most of the washing liquid such as sterile water adhering to the cap 33 is removed, so that it is possible to prevent the trouble that the cap 33 to which sterile water or the like adheres is sent to the cap attachment device 16.

Further, according to the present embodiment, even after sterile air is blown from the air blow nozzle 85, the washing liquid such as sterile water slightly remains in the cap 33. This makes it possible to improve lubrication between the cap 33 and the chute 59 while the cap 33 is conveyed from the washing chamber 55 to the cap attachment device 16 by the chute 59 and to prevent the temperature of the cap 33 from rising due to frictional heat with the chute 59. By suppressing the rise in the temperature of the cap 33 as described above, it is possible to stably perform seaming operation of the cap 33 in the cap attachment device 16. In the cap attachment device 16, sterile air may be blown against the inner surface of the cap 33 to remove washing water remaining in the cap 33. As a result, contamination of the washing water into the bottle 30 can be minimized.

As described above, even when the conveying speed of the cap 33 in the cap sterilizer 50 is increased to 100 cpm or more and 1500 cpm, it is possible to reliably sterilize the cap 33 while preventing the sterilant from leaking from the housing 60.

Second Embodiment

Figure 7:
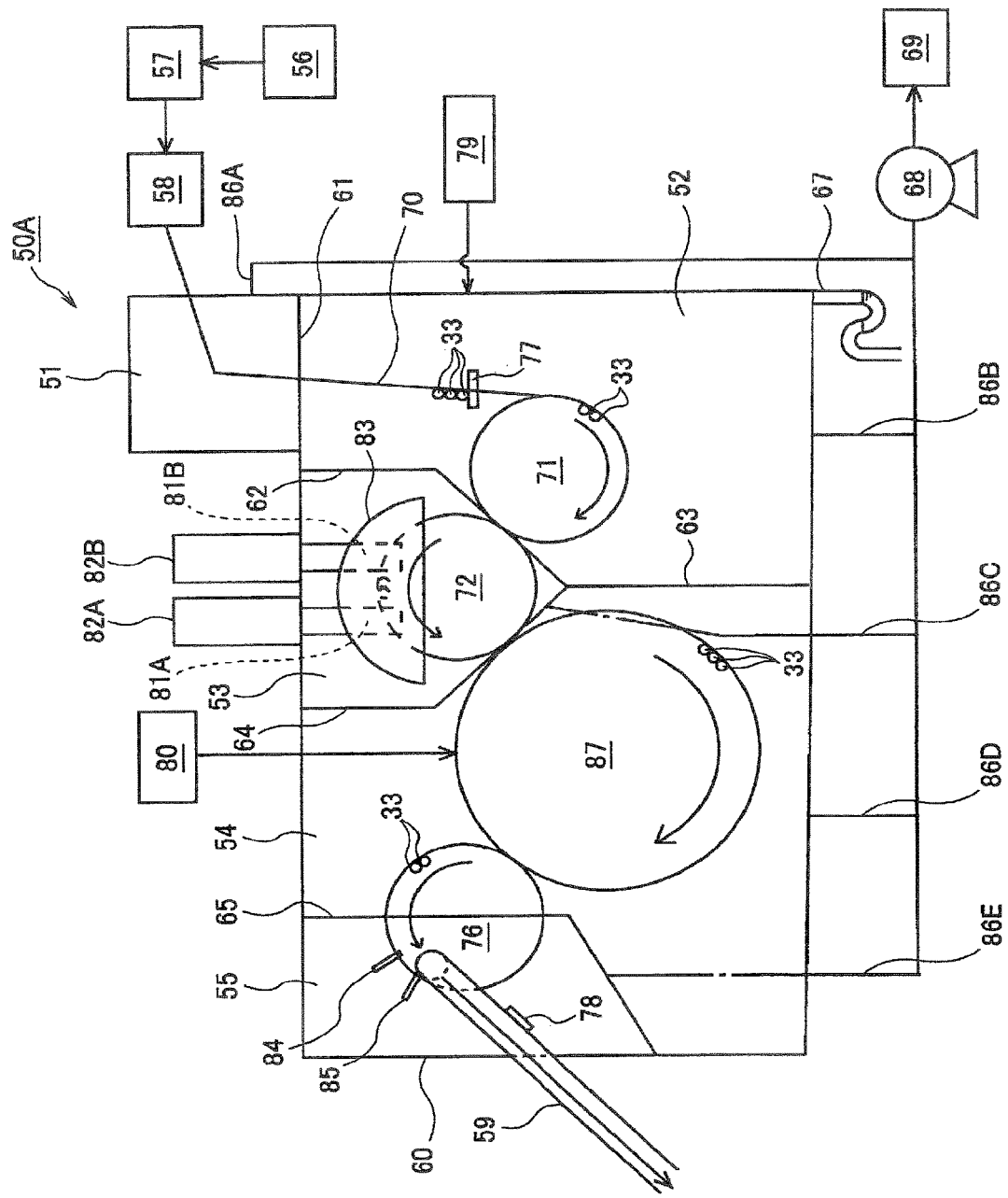
FIG. 7 is a schematic front view illustrating a cap sterilizer according to a second embodiment of the present invention.

Next, a second embodiment of the present invention will be described below with reference to FIG. 7. FIG. 7 is a schematic front view illustrating a cap sterilizer according to the second embodiment of the present invention. In the second embodiment illustrated in FIG. 7, the configuration of the rotation conveyance mechanism in the air rinse chamber 54 is different, and other configurations are substantially the same as those of the first embodiment described above. In FIG. 7, the same portions as those in the first embodiment will be assigned the same reference numerals and will not be described in detail.

In a cap sterilizer 50A illustrated in FIG. 7, a large-sized rotation conveyance mechanism 87 larger than the rotation conveyance mechanisms 71, 72, and 76 is provided in the air rinse chamber 54. The large-sized rotation conveyance mechanism 87 rotates (on its axis) along the axis parallel to the horizontal direction, thereby directly conveying the cap 33 from the second rotation conveyance mechanism 72 to the sixth rotation conveyance mechanism 76. Like the rotation conveyance mechanisms 71, 72, and 76, the large-sized rotation conveyance mechanism 87 may have a star wheel provided with a notch for accommodating the cap 33 and a plurality of rails arranged around the star wheel. Alternatively, the large-sized rotation conveyance mechanism 87 may be constituted by a rotary joint.

According to the present embodiment, the cap sterilizer 50A can be compactly configured. Further, according to the present embodiment, in the air rinse chamber 54, sterile hot air can be supplied while following the large-sized rotation conveyance mechanism 87 such as a rotary joint, so that even with the large-sized cap 33, the temperature can be reliably raised.

Third Embodiment

Figure 8:
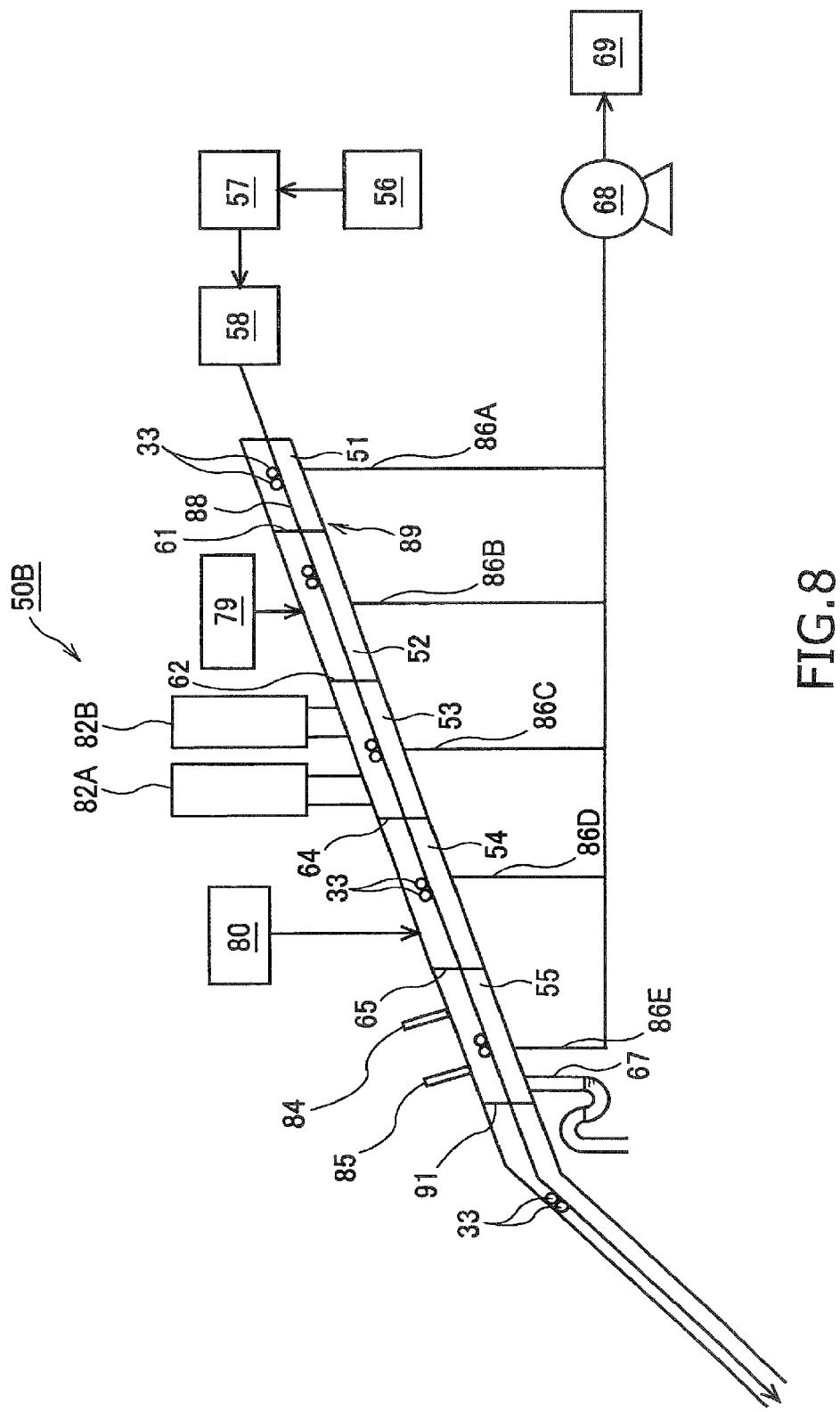
FIG. 8 is a schematic front view illustrating a cap sterilizer according to a third embodiment of the present invention.
Figure 9:
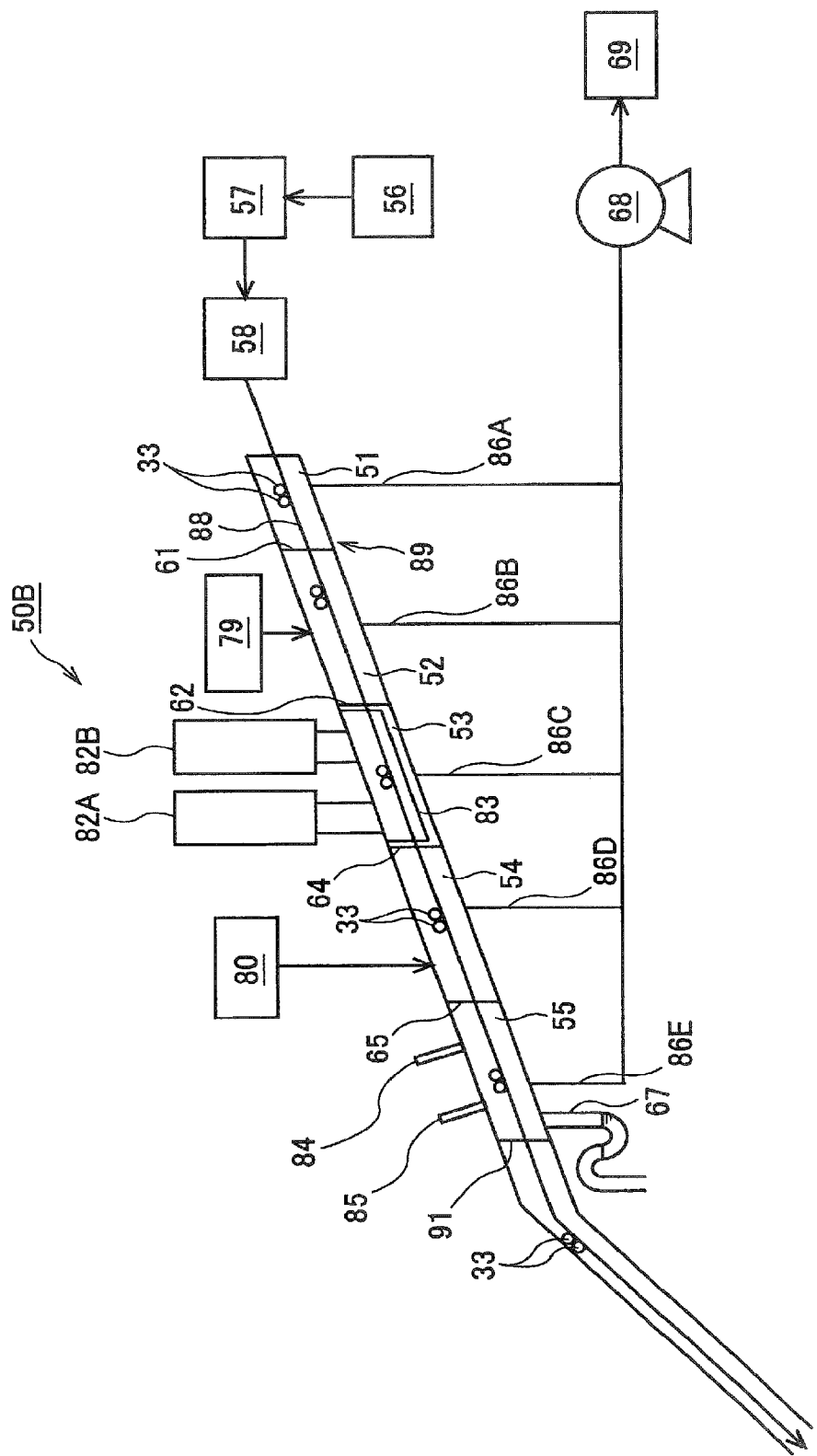
FIG. 9 is a schematic front view illustrating a cap sterilizer according to a modification of the third embodiment of the present invention.

Next, the third embodiment of the present invention will be described below with reference to FIGS. 8 and 9. FIG. 8 is a schematic front view illustrating a cap sterilizer according to the third embodiment of the present invention, and FIG. 9 is a schematic front view illustrating a modification of the cap sterilizer according to the present embodiment. The third embodiment illustrated in FIGS. 8 and 9 is different from the first embodiment in that the cap 33 is mainly conveyed by a chute 88. In FIGS. 8 and 9, the same portions as those in the first embodiment will be assigned the same reference numerals and will not be described in detail.

As illustrated in FIG. 8, a cap sterilizer 50B includes a first infeed chamber 51, a second infeed chamber 52, a sterilant atomizing chamber 53, an air rinse chamber 54, and a washing chamber 55 provided from the upper side to the lower side. The chambers 51, 52, 53, 54, and 55 are arranged inside a cylindrical body 89.

In the chambers 51, 52, 53, 54, and 55, the chute 88 for conveying a plurality of the caps 33 in a row is provided. The chute 88 may include, for example, a plurality of rails. In this case, a space is formed in a region surrounded by the plurality of rails so that the cap 33 does not come off, and the cap 33 is accommodated in this space and conveyed. Although the chute 88 extends substantially linearly in FIG. 8, the present invention is not limited thereto, and the chute 88 may extend in a spiral shape.

The first infeed chamber 51 and the second infeed chamber 52 are separated by a partition wall 61, and the second infeed chamber 52 and the sterilant atomizing chamber 53 are separated by a partition wall 62. In addition, the sterilant atomizing chamber 53 and the air rinse chamber 54 are separated by a partition wall 64, and the air rinse chamber 54 and the washing chamber 55 are separated by a partition wall 65. A partition wall 91 is provided downstream of the washing chamber 55 (on the cap attachment device 16 side).

The cap 33 from the cap inspection machine 58 is introduced into the first infeed chamber 51. The cap 33 from the first infeed chamber 51 is fed to the second infeed chamber 52. Sterile hot air from a first hot air supplier 79 is sent into the second infeed chamber 52.

The sterilant atomizing chamber 53 sprays a sterilant against the cap 33 fed from the second infeed chamber 52. In the second infeed chamber 52, the sterilant is sprayed against the cap 33 while the cap 33 is conveyed by the chute 88. The air rinse chamber 54 air-rinses the cap 33 sprayed with the sterilant in the sterilant atomizing chamber 53. The cap 33 is conveyed by the chute 88 in the air rinse chamber 54, and meanwhile, sterile hot air is blown against the inner and outer surfaces of the cap 33. As illustrated in FIG. 9, an elongated cover 83 covering surroundings of spray nozzles 81A and 81B may be provided in the sterilant atomizing chamber 53.

The washing chamber 55 washes the cap 33 which has been air-rinsed in the air rinse chamber 54. In the washing chamber 55, the cap 33 is first blown with sterile water by a washing nozzle 84 and then blown with sterile air by an air blow nozzle 85 to remove the sterile water. The washing chamber 55 may not be provided.

The cap 33 carried from the washing chamber 55 is sent to the cap attachment device 16 by the chute 88.

According to the present embodiment, the cap 33 can be sterilized by modifying an existing facility (such as the chute 88), so that it is possible to efficiently use the existing facility.

Fourth Embodiment

Figure 10:
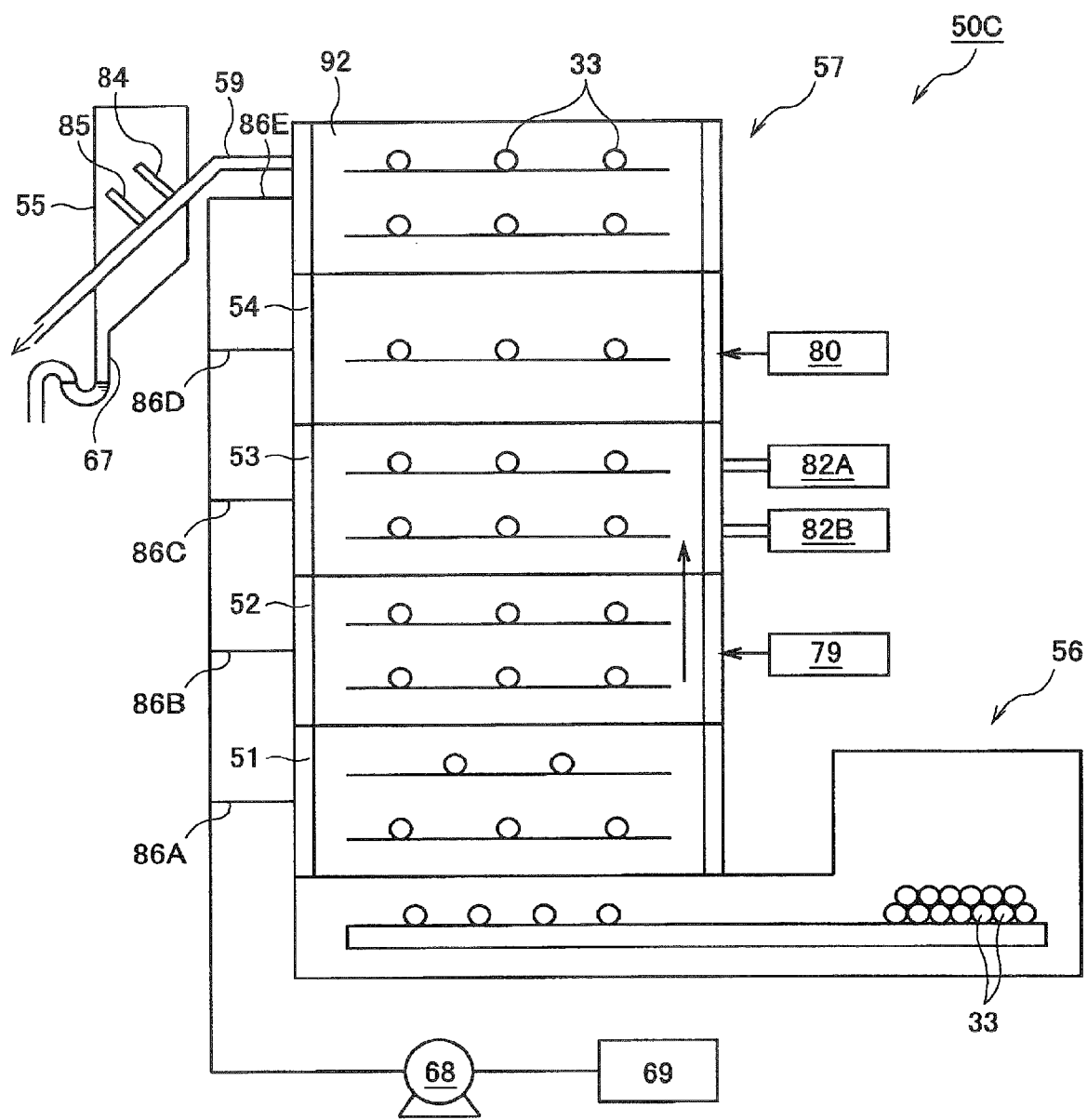
FIG. 10 is a schematic front view illustrating a cap sterilizer according to a fourth embodiment of the present invention.
Figure 11:
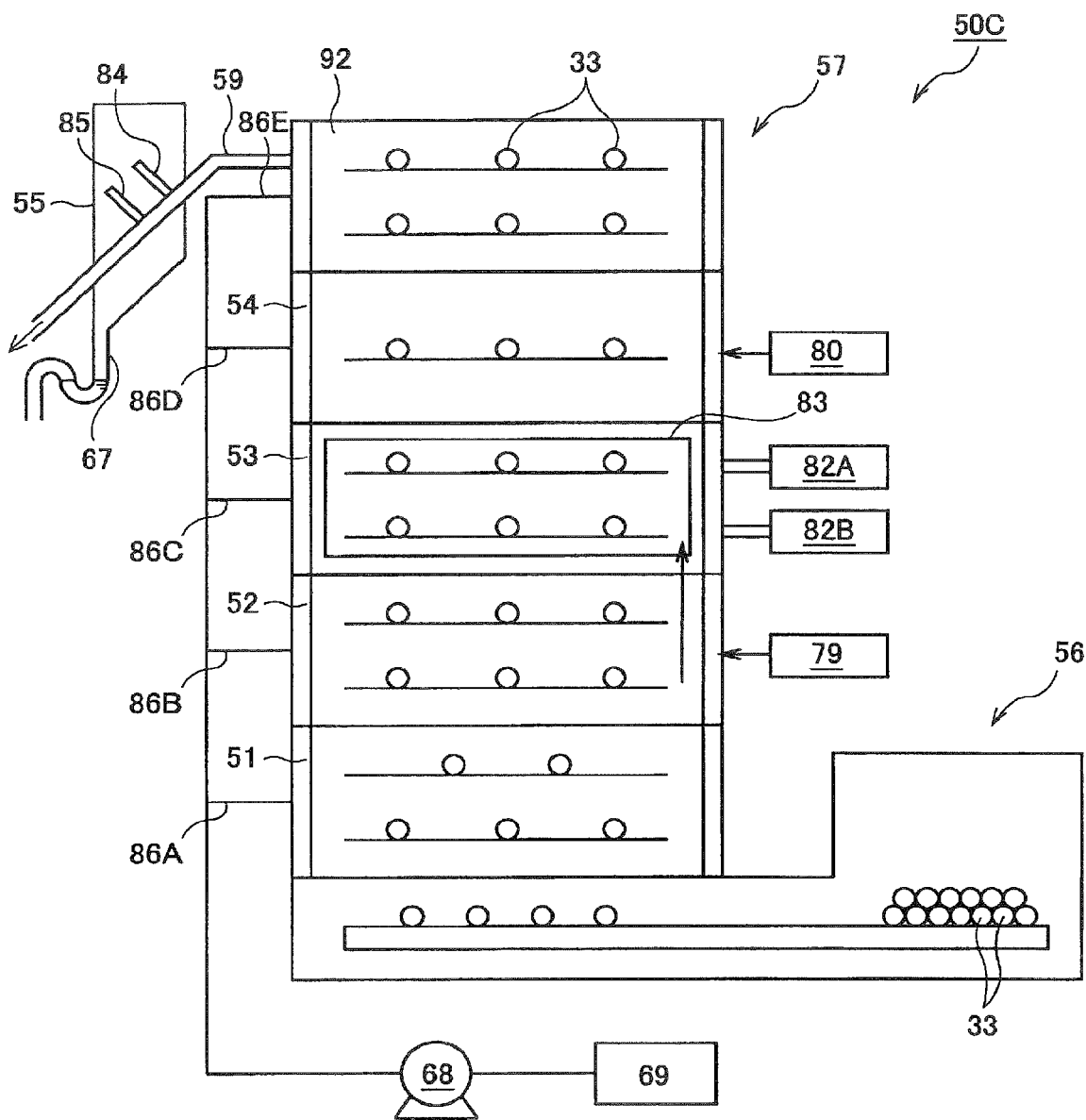
FIG. 11 is a schematic front view illustrating a cap sterilizer according to a modification of the fourth embodiment of the present invention.

Next, the fourth embodiment of the present invention will be described below with reference to FIGS. 10 and 11. FIG. 10 is a schematic front view illustrating a cap sterilizer according to the fourth embodiment of the present invention, and FIG. 11 is a schematic front view illustrating a modification of the cap sterilizer according to the present embodiment. The fourth embodiment illustrated in FIGS. 10 and 11 is different from the first embodiment in that the cap 33 is sterilized using a sorter 57. In FIGS. 10 and 11, the same portions as those in the first embodiment will be assigned the same reference numerals and will not be described in detail.

As illustrated in FIG. 10, a cap sterilizer 50C is provided in the sorter 57. The cap sterilizer 50C includes a first infeed chamber 51, a second infeed chamber 52, a sterilant atomizing chamber 53, and an air rinse chamber 54 provided from the lower side to the upper side.

In the chambers 51, 52, 53, and 54, a conveyor 92 for conveying a plurality of the caps 33 from the lower side to the upper side is provided. The conveyor 92 is, for example, of an endless type, and conveys the cap 33 from a hopper 56 to a chute 59 via the sorter 57 while circulating vertically. The chute 59 is provided with the washing chamber 55, and a drainage pipe 67 is connected to the washing chamber 55. The washing chamber 55 is not necessarily provided.

The cap 33 from the hopper 56 is introduced into the first infeed chamber 51. The cap 33 from the first infeed chamber 51 is fed to the second infeed chamber 52. Sterile hot air from a first hot air supplier 79 is sent into the second infeed chamber 52.

The sterilant atomizing chamber 53 sprays a sterilant against the cap 33 fed from the second infeed chamber 52. In the second infeed chamber 52, the sterilant is sprayed against the cap 33 which is being raised by the conveyor 92. The air rinse chamber 54 air-rinses the cap 33 sprayed with the sterilant in the sterilant atomizing chamber 53. The cap 33 is conveyed by the conveyor 92 in the air rinse chamber 54, and meanwhile, sterile hot air is blown against the inner and outer surfaces of the cap 33. As illustrated in FIG. 11, a rectangular cover 83 covering surroundings of spray nozzles 81A and 81B may be provided in the sterilant atomizing chamber 53.

The cap 33 carried from the air rinse chamber 54 is sent to the cap attachment device 16 by the chute 59 via the washing chamber 55.

The washing chamber 55 washes the cap 33 which has been air-rinsed in the air rinse chamber 54. In the washing chamber 55, the cap 33 is first blown with sterile water by a washing nozzle 84 and then blown with sterile air by an air blow nozzle 85 to remove the sterile water.

According to the present embodiment, the cap sterilizer 50C can be compactly configured. In the present embodiment, the chamber is not necessarily provided.

Fifth Embodiment

Figure 12:
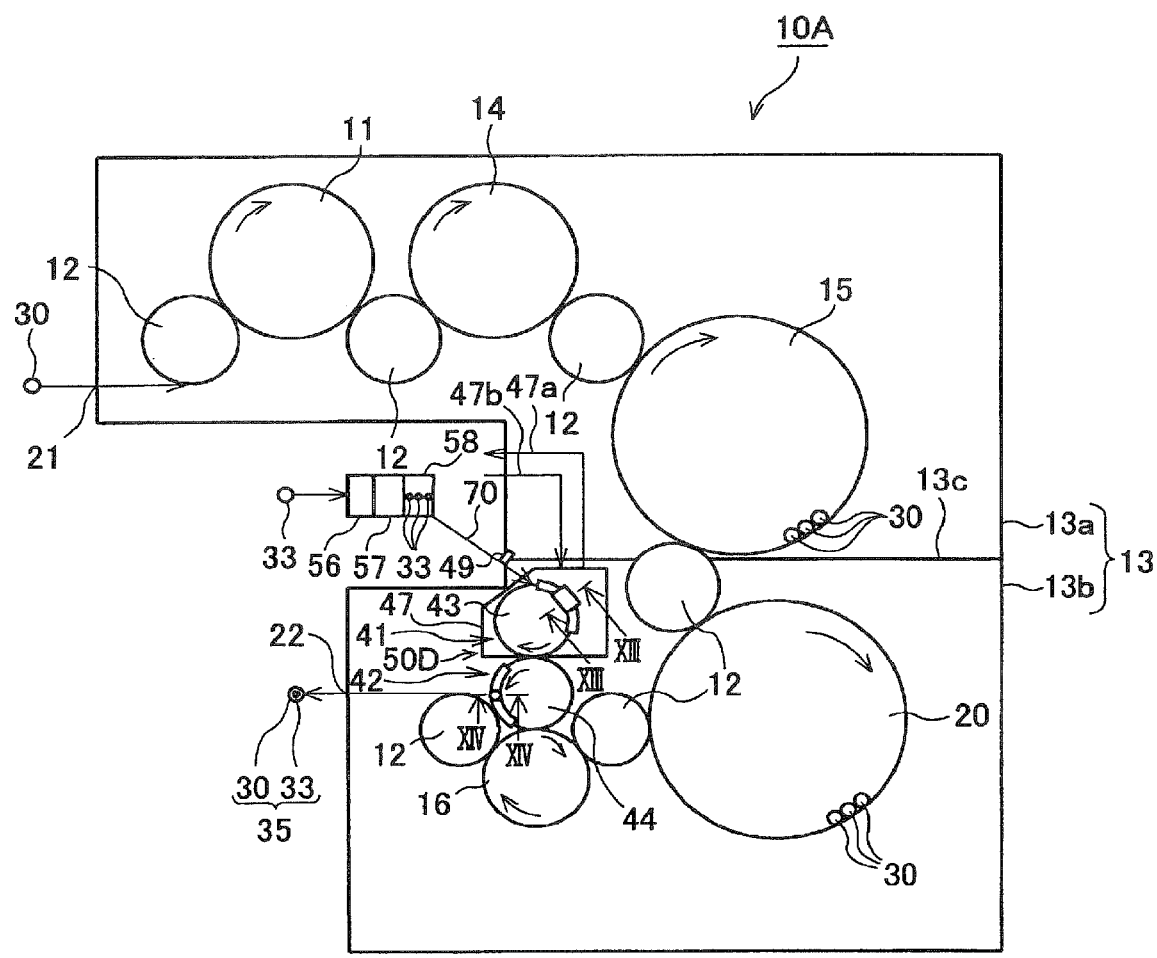
FIG. 12 is a schematic plan view illustrating a content filling system according to a fifth embodiment of the present invention.
Figure 13:
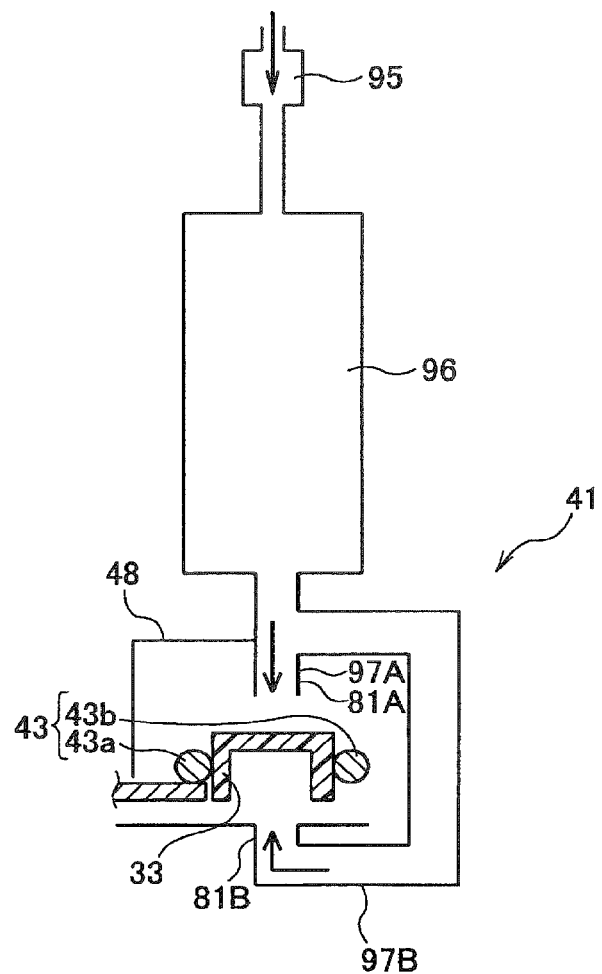
FIG. 13 is a schematic cross-sectional view (cross-sectional view taken along the line XIII-XIII in FIG. 12) illustrating a sterilant atomizing wheel of a cap sterilizer according to the fifth embodiment of the present invention.
Figure 14:
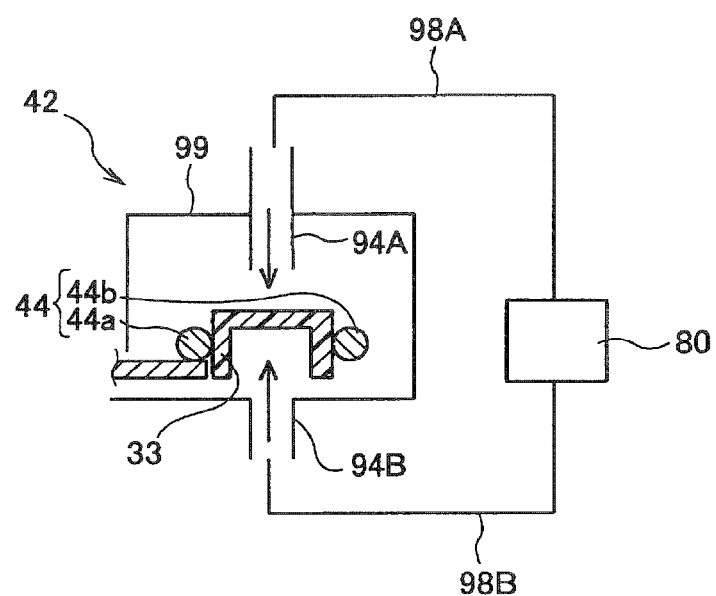
FIG. 14 is a schematic cross-sectional view (cross-sectional view taken along the line XIV-XIV in FIG. 12) illustrating an air rinse wheel of the cap sterilizer according to the fifth embodiment of the present invention.

Next, a fifth embodiment of the present invention will be described below with reference to FIGS. 12 to 14. FIGS. 12 to 14 illustrate the fifth embodiment of the present invention. In FIGS. 12 to 14, the same portions as those in the first to fourth embodiments will be assigned the same reference numerals and will not be described in detail.

(Content Filling System)

First, a content filling system (sterile filling system, aseptic filling system) according to the present embodiment will be described with reference to FIG. 12.

A content filling system 10A illustrated in FIG. 12 is a system for filling a bottle (container) 30 with a content such as a beverage. The configuration of the bottle 30 is substantially the same as that of the first to fourth embodiments.

As illustrated in FIG. 12, the content filling system 10A includes a bottle feeding portion 21, a sterilizer (bottle sterilizer) 11, an air rinse device 14, a sterile water rinse device 15, a filling device (filler) 20, a cap attachment device (a capper, a seamer, and a capping machine) 16, and a product bottle conveyor 22. These bottle feeding portion 21, sterilizer 11, air rinse device 14, sterile water rinse device 15, filling device 20, cap attachment device 16, and product bottle conveyor 22 are disposed in this order along a conveying direction of the bottle 30 from an upstream side to a downstream side. Between the sterilizer 11, the air rinse device 14, the sterile water rinse device 15, the filling device 20, and the cap attachment device 16, a plurality of convey wheels 12 for conveying the bottle 30 between these devices is provided.

The configurations of the bottle feeding portion 21, the sterilizer 11, the air rinse device 14, the sterile water rinse device 15, the filling device 20, the cap attachment device 16, and the product bottle conveyor 22 are substantially similar to the configurations in the first to fourth embodiments.

The cap 33 is sterilized by the cap sterilizer 50D in advance. The cap sterilizer 50D is disposed inside a sterile chamber 13 (to be described later) and near the cap attachment device 16, for example. In the cap sterilizer 50D, the caps 33 carried in from the outside of the sterile chamber 13 are sequentially conveyed toward the cap attachment device 16. Mist or gas of hydrogen peroxide is blown against inner and outer surfaces of the cap 33 on the way of conveyance of the cap 33 toward the cap attachment device 16 and then the cap 33 is dried with hot air and sterilized. The configuration of the cap sterilizer 50D thus configured will be described later.

The sterilizer 11, the air rinse device 14, the sterile water rinse device 15, the filling device 20, the cap attachment device 16, and the cap sterilizer 50D each have a wheel. The sterilizer 11, the air rinse device 14, the sterile water rinse device 15, the filling device 20, the cap attachment device 16, and the cap sterilizer 50D are connected to each other by the wheels (a conveyance wheel 12, each wheel of the sterilizer 11, the air rinse device 14, the sterile water rinse device 15, the filling device 20, and the cap attachment device 16, and a sterilant atomizing wheel 41 and an air rinse wheel 42 of the cap sterilizer 50D).

In addition, the content filling system 10A includes the sterile chamber 13. The sterile chamber 13 houses the sterilizer 11, the air rinse device 14, the sterile water rinse device 15, the filling device 20, the cap attachment device 16, and the cap sterilizer 50D which have been described above. This content filling system 10A may be, for example, a sterile filling system. In this case, the interior of the sterile chamber 13 is kept in a sterile state.

In addition, the sterile chamber 13 is partitioned into a bottle sterile chamber 13a and a filling/seaming chamber 13b. A chamber wall 13c is provided between the bottle sterile chamber 13a and the filling/seaming chamber 13b, and the bottle sterile chamber 13a and the filling/seaming chamber 13b are adjacent to each other with the chamber wall 13c interposed therebetween. In the bottle sterile chamber 13a, the sterilizer 11, the air rinse device 14, and the sterile water rinse device 15 are arranged. In the filling/seaming chamber 13b, the filling device 20, the cap attachment device 16, and the cap sterilizer 50D are arranged. In this embodiment, although the chamber wall 13c is provided between the bottle sterile chamber 13a, the filling/seaming chamber 13b and a cap sterilization chamber 47 (described later), a chamber wall may be provided for each wheel.

Alternatively, the content filling system 10A may be a high temperature filling system that fills a content at a high temperature of 85° C. or more and less than 100° C. The content filling system 10 may also be a medium temperature filling system that fills a content at a medium temperature of 55° C. or more and less than 85° C.

(Cap Sterilizer)

Next, with reference to FIGS. 12 to 14, the configuration of the cap sterilizer 50D described above and a mechanism used to convey the cap 33 to the cap sterilizer 50D will be described.

As illustrated in FIG. 12, the cap sterilizer 50D includes the sterilant atomizing wheel 41 and the air rinse wheel 42. The sterilant atomizing wheel 41 and the air rinse wheel 42 are arranged in this order along the conveying direction of the cap 33. In FIG. 12, the sterilant atomizing wheel 41 and the air rinse wheel 42 are each constituted by one wheel, but the present invention is not limited thereto, and the sterilant atomizing wheel 41 and/or the air rinse wheel 42 may include a plurality of wheels.

A hopper 56, a sorter 57, and a cap inspection machine 58 are provided on the previous process side of the sterilant atomizing wheel 41 and outside the sterile chamber 13. A large number of the caps 33 are randomly charged into the hopper 56 from the outside. The sorter 57 arranges the caps 33, randomly charged into the hopper 56, in one row or multiple rows and conveys the caps 33 from a lower side to an upper side in the vertical direction. The cap inspection machine 58 inspects the shape and the like of each of the caps 33 and discharges the caps 33 failed in inspection. The caps 33 which have passed the inspection are conveyed in a row toward the cap sterilizer 50D disposed inside the sterile chamber 13.

The cap 33 is a well-known one and has a substantially circular planar shape with an opening on the inner surface side. As the cap 33, one formed of a thermoplastic resin such as high density polyethylene (HDPE), polypropylene (PP), and biodegradable plastic can be used. As the cap 33, in addition to a normal bottle cap, a composite cap or a sport cap may be used.

Between the cap inspection machine 58 and the cap sterilizer 50D, a conveyance guide 70 for conveying a plurality of the caps 33 in a row is provided. The conveyance guide 70 may include, for example, a plurality of rails. In this case, a space is formed in a region surrounded by the plurality of rails so that the cap 33 does not come off, and the cap 33 is accommodated in this space and conveyed. The cap 33 is transferred from the cap inspection machine 58 side toward the cap sterilizer 50D by its own weight. By providing the conveyance guide 70 thus configured, it is possible to convey the cap 33 at high speed from the cap inspection machine 58 to the cap sterilizer 50D. The conveyance guide 70 is provided with an openable and closable stopper 49. When the stopper 49 is opened, the cap 33 is sent to the cap attachment device 16 via the conveyance guide 70. On the other hand, when the stopper 49 is closed, the cap 33 stays at this position. The cap 33 may be conveyed at high speed by using compressor air or a conveyer (or a combination thereof) as the conveyance guide 70.

The sterilant atomizing wheel 41 conveys the cap 33 while rotating (revolving) and at the same time sprays the sterilant against the cap 33 being conveyed. The sterilant atomizing wheel 41 is disposed adjacent to the air rinse wheel 42. A wheel (not illustrated) which causes the sterilant to stay while adhering the sterilant between the sterilant atomizing wheel 41 and the air rinse wheel 42 may be provided without changing the order of the sterilant atomizing wheel 41 and the air rinse wheel 42.

As illustrated in FIG. 13, the sterilant atomizing wheel 41 has a first rotating mechanism 43 which conveys the cap 33 while rotating and spray nozzles 81A and 81B which blow a sterilant against the cap 33 rotated and conveyed by the first rotating mechanism 43. The first rotating mechanism 43 rotates (on its axis) along an axis parallel to the vertical direction, thereby rotating (revolving) and conveying the plurality of the caps 33. The first rotating mechanism 43 has a star wheel 43a located at the center and provided with a notch for accommodating the cap 33 and a plurality of rails 43b arranged around the star wheel 43a and preventing the cap 33 from coming off. The cap 33 is conveyed as the star wheel 43a is driven, guided by the rail 43b, and rotated (revolved). By using the first rotating mechanism 43 thus configured, it is possible to convey the cap 33 at high speed within the sterilant atomizing wheel 41.

The sterilant supplied by the sterilant atomizing wheel 41 is, for example, hydrogen peroxide solution. The cap 33 sent from the conveyance guide 70 (see FIG. 12) is delivered to the star wheel 43a, and while the cap 33 is conveyed by the star wheel 43a, the sterilant is sprayed by the spray nozzles 81A and 81B. A supply spray 95 which supplies a sterilant and a heater 96 which heats the sterilant from the supply spray 95 are provided above the first rotating mechanism 43. A first supply pipe 97A and a second supply pipe 97B which branch and supply the sterilant are connected to the heater 96. Among the supply pipes, the first supply pipe 97A is connected to the spray nozzle 81A for outer surface which supplies the sterilant to the outer surface (top surface portion) side of the cap 33. On the other hand, the second supply pipe 97B is connected to the spray nozzle 81B for inner surface which supplies the sterilant to the inner surface (opening) side of the cap 33. For example, a tunnel 48 having a substantially arc shape in plan view is disposed above the rail 43b and around the spray nozzles 81A and 81B. The tunnel 48 covers the surroundings of the spray nozzles 81A and 81B, prevents the sterilant from the spray nozzles 81A and 81B from scattering to the surroundings, and enables effective spraying of the sterilant to the cap 33.

An adhesion amount of hydrogen peroxide necessary for sterilizing the cap 33 is 0.6 μL/cm$^2$ or more and 4.7 μL/cm$^2$ or less (preferably 1.2 μL/cm$^2$ or more and 2.4 μL/cm$^2$ or less) in terms of 35% by weight. Within this range, the cap 33 can be sterilized at high speed, and a medicine can be reliably removed by air rinsing to be described later.

As the sterilant, besides hydrogen peroxide, alcohols such as peracetic acid, nitric acid, chlorine sterilant, sodium hydroxide, potassium hydroxide, ethyl alcohol, and isopropyl alcohol, chlorine dioxide, ozone water, acid water, and surfactant may be used alone, or two or more of these may be used in combination at any ratio.

Referring to FIG. 12, the air rinse wheel 42 conveys the cap 33 sprayed with the sterilant in the sterilant atomizing wheel 41 while rotating (revolving) and at the same time air-rinses the cap 33 being conveyed. The air rinse wheel 42 is disposed adjacent to the cap attachment device 16.

As illustrated in FIG. 14, the air rinse wheel 42 has a second rotating mechanism 44 which conveys the cap 33 while rotating and air rinse nozzles 94A and 94B which blow sterile hot air against the cap 33 rotated and conveyed by the second rotating mechanism 44. The second rotating mechanism 44 rotates (on its axis) along the axis parallel to the vertical direction, thereby rotating (revolving) and conveying the plurality of the caps 33. The second rotating mechanism 44 has a star wheel 44a located at the center and provided with a notch for accommodating the cap 33 and a plurality of rails 44b arranged around the star wheel 44a and preventing the cap 33 from coming off. The cap 33 is conveyed as the star wheel 44a is driven, guided by the rail 44b, and rotated (revolved). By using the second rotating mechanism 44 thus configured, it is possible to convey the cap 33 at high speed within the air rinse wheel 42.

The cap 33 is sequentially conveyed by the second rotating mechanism 44 in the air rinse wheel 42, and meanwhile, sterile hot air is blown against the inner and outer surfaces of the cap 33. Sterile hot air from a hot air supplier 80 located outside the sterile chamber 13 is sent to the air rinse wheel 42. A first air supply path 98A and a second air supply path 98B through which sterile hot air is supplied are connected to the hot air supplier 80. Among the air supply paths, the first air supply path 98A is connected to the air rinse nozzle 94A for outer surface which supplies sterile hot air to the outer surface (top surface portion) side of the cap 33. On the other hand, the second air supply path 98B is connected to the air rinse nozzle 94B for inner surface which supplies sterile hot air to the inner surface (opening) side of the cap 33. The air rinse nozzles 94A and 94B blow out sterile hot air supplied from the hot air supplier 80 via the air supply paths 98A and 98B. In addition, for example, a cover 99 having a substantially arc shape in plan view is disposed above the rail 44b and around the air rinse nozzles 94A and 94B. The cover 99 covers the surroundings of the air rinse nozzles 94A and 94B and prevents the sterilant blown off by sterile hot air from the air rinse nozzles 94A and 94B from scattering to the surroundings. The air rinse nozzles 94A and 94B may be fixed pipes or may blow hot air while following the cap 33 by using a rotary joint. An additional hot air nozzle may be preliminarily provided at a downstream position on the sterilant atomizing wheel 41. In addition, in order to shorten the sterilization time of the cap 33, a preheating wheel (not illustrated) may be provided on the upstream side of the sterilant atomizing wheel 41.

The temperature of sterile hot air is, for example, 80° C. or more and 140° C. or less, preferably 90° C. or more and 120° C. or less. The air volume of sterile hot air is, for example, 5 m$^3$/min or more and 20 m$^3$/min or less. The sterile hot air blowing time is 0.5 seconds or more and 20 seconds or less, preferably 1 second or more and 14 seconds or less. By blowing sterile hot air against the cap 33, the temperature of the cap 33 is raised to 40° C. or more, preferably 50° C. or more. As a result, the sterilant adhering to the cap 33 is removed. Sterile hot air may contain a trace amount of a component of a sterilant such as hydrogen peroxide. As described above, in the air rinse wheel 42, sterile hot air is blown against the cap 33 from the air rinse nozzles 94A and 94B. This makes it possible to reliably remove the sterilant adhering to the cap 33 in the sterilant atomizing wheel 41.

Thus, the cap 33 from which the sterilant has been removed by sterile hot air at the air rinse wheel 42 is delivered to the cap attachment device 16. Thereafter, in the cap attachment device 16, the cap 33 delivered from the cap sterilizer 50D is attached to the mouth of the bottle 30.

Throughout the cap sterilizer 50D, the conveying speed of the cap 33 is 100 cpm or more and 1500 cpm or less, preferably 500 cpm or more and 1000 cpm or less. According to the cap sterilizer 50D according to the present embodiment, even when the cap 33 is conveyed at high speed as described above, the cap 33 can be sterilized reliably. The number of the caps 33 passing through a predetermined position per minute is represented by cap per minute (cpm). When the filling speed of the bottle 30 is slow, such as when the bottle 30 is a large size bottle (having an inner capacity of 1 L or more), the conveying speed of the cap 33 may be made slower than the above speed in accordance with this filling speed. In this case, supply conditions (temperature, flow rate, etc.) of hot air in the air rinse wheel 42 may be adjusted so that the temperature of the cap 33 does not rise.

In the sterilant atomizing wheel 41 and the air rinse wheel 42, since the unsterilized cap 33 (the cap 33 in the step of being sterilized) is introduced into the sterile chamber 13, it is preferable to cover these wheels 41 and 42 (at least the sterilant atomizing wheel 41) with another chamber so that bacteria do not contaminate a filling/seaming area. For example, as illustrated in FIG. 12, the sterilant atomizing wheel 41 may be covered with the cap sterilization chamber 47. An air supply line 47a and an exhaust line 47b are connected to the cap sterilization chamber 47. The air supply line 47a and the exhaust line 47b communicate with the outside of the sterile chamber 13, and clean air is supplied and exhausted between the outside and the cap sterilization chamber 47. The internal pressure (positive pressure) of the cap sterilization chamber 47 is controlled to be lower than the internal pressure of the filling/seaming chamber 13b. As a result, it is possible to prevent bacteria adhering to the unsterilized cap 33 (the cap 33 in the step of being sterilized) from entering the filling/seaming chamber 13b. It is preferable that the pressure of the bottle sterile chamber 13a is similarly lower than the pressure of the filling/seaming chamber 13b.

(Content Filling Method)

Next, a content filling method using the above-described content filling system 10A (FIG. 12) will be described. In the following description, a filling method at a normal time, that is, a content filling method in which a content such as a beverage is filled inside the bottle 30 to produce the product bottle 35 will be described.

In a manner substantially similar to the cases of the first to fourth embodiments, first, the bottle 30 sequentially passes through the bottle feeding portion 21, the sterilizer 11, the air rinse device 14, and the filling device 20, and a content is filled therein.

Subsequently, the bottle 30 filled with the content by the filling device 20 is conveyed to the cap attachment device 16 by the convey wheel 12.

On the other hand, the cap 33 is sterilized by the cap sterilizer 50D illustrated in FIG. 12 in advance (cap sterilization step). Meanwhile, first, a large number of the caps 33 are randomly charged into the hopper 56 located outside the cap sterilizer 50D. Then, the caps 33 randomly charged into the hopper 56 are aligned by the sorter 57 and then conveyed to the cap inspection machine 58. Then, in the cap inspection machine 58, the shape and the like of each of the caps 33 are inspected, and the caps 33 which have passed the inspection are conveyed in a row toward the cap sterilizer 50D by the conveyance guide 70.

The cap 33 introduced into the cap sterilizer 50D is delivered to the sterilant atomizing wheel 41. Subsequently, in the sterilant atomizing wheel 41, while the cap 33 is rotated and conveyed by the first rotating mechanism 43, a sterilant such as a hydrogen peroxide solution is sprayed from the spray nozzles 81A and 81B, and the inner and outer surfaces of the cap 33 are sterilized (sterilant spray step).

Subsequently, the cap 33 sprayed with the sterilant is delivered to the air rinse wheel 42. In the air rinse wheel 42, the cap 33 is rotated and conveyed by the second rotating mechanism 44, and meanwhile, sterile hot air is blown against the inner and outer surfaces of the cap 33 (air-rinsing step). As a result, the sterilant adhering to the cap 33 is air-rinsed. Thereafter, the cap 33 is delivered from the air rinse wheel 42 to the cap attachment device 16.

The cap 33 sterilized by the cap sterilizer 50D as described above is attached to the mouth of the bottle 30 which has been conveyed from the filling device 20 in the cap attachment device 16. Consequently, the product bottle 35 having the bottle 30 and the cap 33 is obtained (cap attaching step).

Thereafter, the product bottle 35 is conveyed from the cap attachment device 16 to the product bottle conveyor 22 and is carried toward the outside of the content filling system 10A.

The respective steps from the sterilization step to the cap attachment step are performed in a sterile atmosphere surrounded by the sterile chamber 13, that is, in a sterile environment. After the sterilization treatment, aseptic air of positive pressure is supplied into the sterile chamber 13 so that the aseptic air is always blown toward the exterior of the sterile chamber 13.

The production (conveying) speed of the bottle 30 in the content filling system 10A is preferably 100 bpm or more and 1500 bpm or less. Here, the conveying speed of the bottle 30 per minute is represented by bottle per minute (bpm).

As described above, according to the present embodiment, the cap sterilizer 50D includes the sterilant atomizing wheel 41, which conveys the cap 33 while rotating and, at the same time, sprays a sterilant against the cap 33 being conveyed, and the air rinse wheel 42 which conveys the cap 33 while rotating and, at the same time, air-rinses the cap 33 being conveyed. As a result, since conveyance of the cap 33 and sterilization and air-rinsing of the cap 33 can be continuously performed, the conveying speed of the cap 33 can be increased, and, at the same time, the cap 33 can be efficiently sterilized.

Further, according to the present embodiment, at the air rinse wheel 42, sterile hot air is blown against both the inner and outer surfaces of the cap 33 by the air rinse nozzles 94A and 94B.

Thus, at the sterilant atomizing wheel 41, the sterilant adhering to the inner and outer surfaces of the cap 33 can be reliably removed by the spray nozzles 81A and 81B. Accordingly, the high concentration of the sterilant can be blown against the cap 33 in the sterilant atomizing wheel 41, and as a result, the conveying speed of the cap 33 can be increased.

Further, according to the present embodiment, since both the cap sterilizer 50D and the cap attachment device 16 are disposed in the sterile chamber 13, the entire content filling system 10A can be compactly configured.

In the present embodiment, the cap sterilizer 50D is installed on the same plane as the plane on which the filling device 20 and the cap attachment device 16 are arranged, but the present invention is not limited thereto, and the cap sterilizer 50D may be installed above the cap attachment device 16.

Modification

Figure 15:
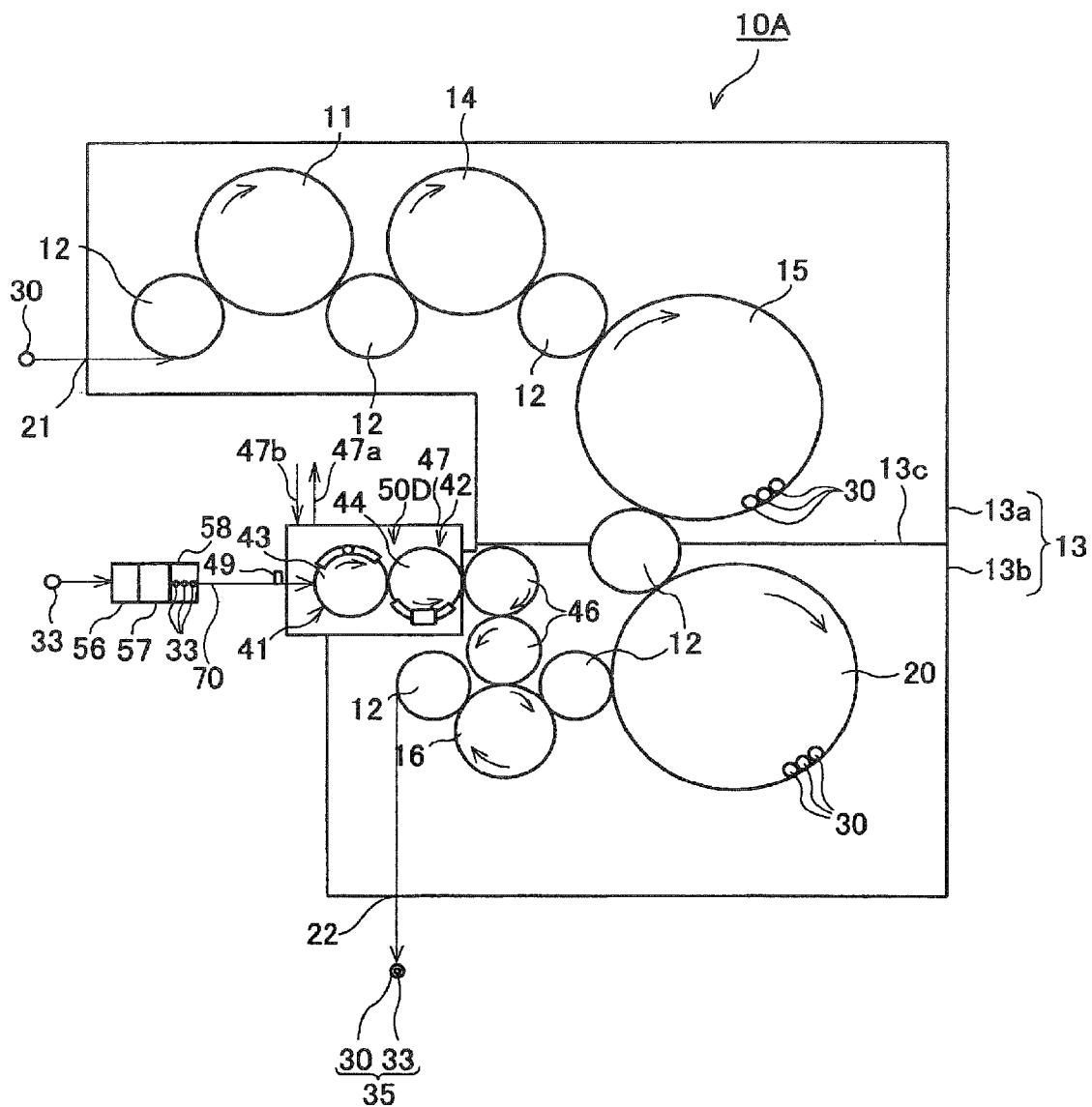
FIG. 15 is a schematic plan view illustrating a content filling system according to a modification (Modification 1) of the fifth embodiment of the present invention.
Figure 16:
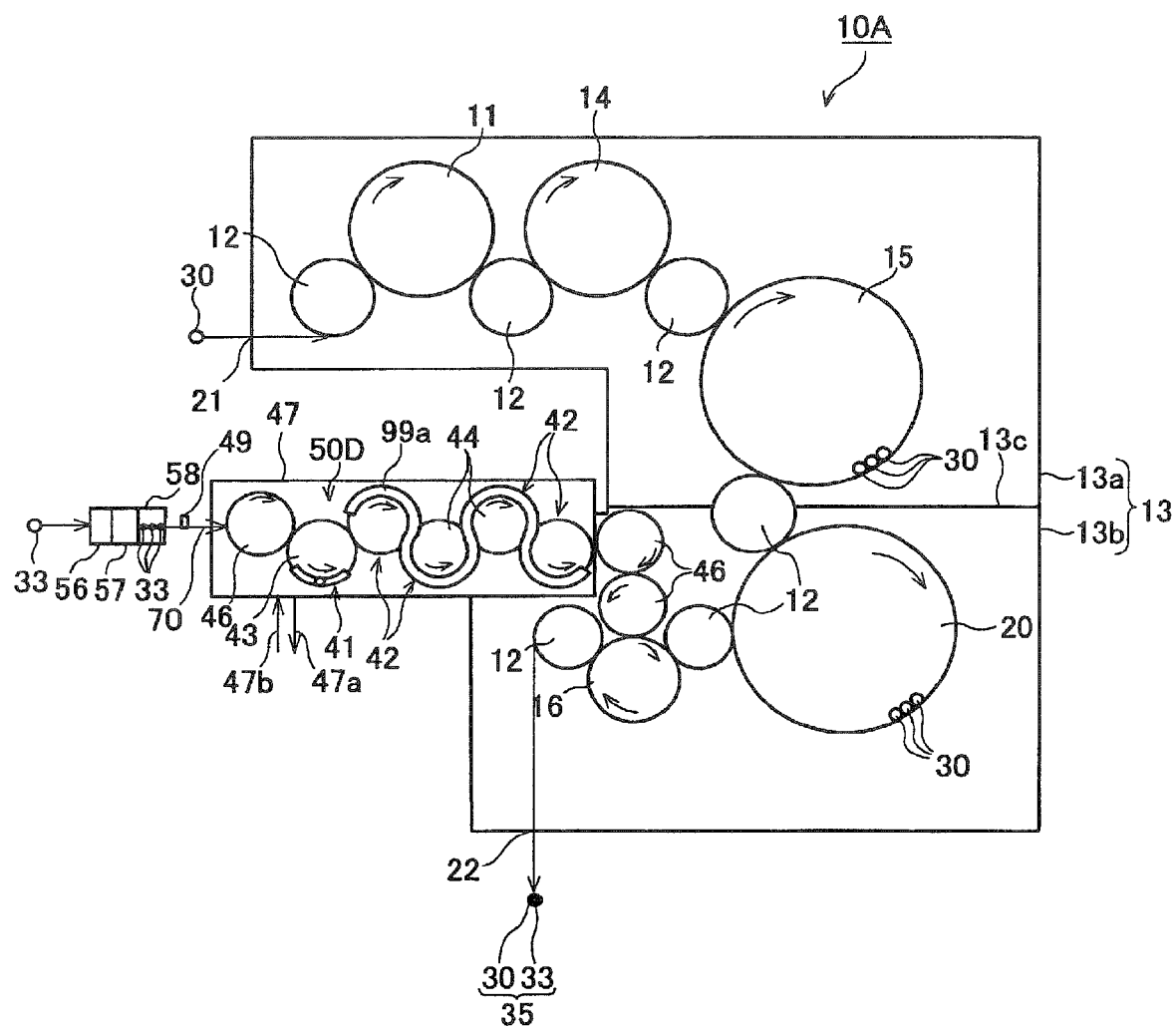
FIG. 16 is a schematic plan view illustrating a content filling system according to a modification (Modification 2) of the fifth embodiment of the present invention.

Next, a modification of the content filling system according to the fifth embodiment will be described with reference to FIGS. 15 and 16. In FIGS. 15 and 16, the same portions as those in the embodiment illustrated in FIGS. 12 to 14 will be assigned the same reference numerals and will not be described in detail.

FIG. 15 is a plan view (view corresponding to FIG. 12) illustrating the content filling system 10A according to a modification (Modification 1) of the present embodiment. In FIG. 15, unlike the embodiment illustrated in FIGS. 12 to 14, the cap sterilization chamber 47 is located outside the sterile chamber 13, and the cap sterilization chamber 47 and the sterile chamber 13 are arranged adjacent to each other. The cap 33 carried from the cap sterilization chamber 47 is conveyed to the cap attachment device 16 by a cap conveyance wheel 46.

FIG. 16 is a plan view (view corresponding to FIG. 12) illustrating the content filling system 10A according to a modification (Modification 2) of the present embodiment. In FIG. 16, unlike Modification 1 illustrated in FIG. 15, a plurality of air rinse wheels 42 is provided, and a cover 99a is provided to straddle the plurality of air rinse wheels 42. The cover 99a meanders in plan view along the traveling direction of the cap 33. As the cap 33 moves inside the cover 99a, sterile hot air is blown against the cap 33.

One wheel may be provided instead of the plurality of the air rinse wheels 42, and this wheel may be provided with an upper rotary joint (not illustrated) to blow hot air against the cap 33 with an air rinse nozzle following the cap 33.

It is preferable to sterilize the above-described cap sterilizers (cap conveyors/sterilizers) 50A, 50B, 50C, and 50D with hydrogen peroxide or a peracetic acid detergent before actually carrying out production using the cap 33.

The invention claimed is:

1. A cap sterilizer comprising:
   an infeed chamber;
   a sterilant atomizing chamber configured to spray a sterilant against a cap fed from the infeed chamber; and
   an air rinse chamber configured to air-rinse the cap after being sprayed with the sterilant in the sterilant atomizing chamber,
   wherein the infeed chamber, the sterilant atomizing chamber, and the air rinse chamber are arranged in this order along a conveying direction of the cap,
   at least the infeed chamber and the air rinse chamber are configured to be exhausted,
   an interior of the infeed chamber, an interior of the sterilant atomizing chamber and an interior of the air rinse chamber are configured to be maintained at a positive pressure, and
   an exhaust pressure in the infeed chamber and an exhaust pressure in the air rinse chamber are higher than an exhaust pressure in the sterilant atomizing chamber, or the sterilant atomizing chamber is not exhausted.

2. The cap sterilizer according to claim 1, wherein the exhaust pressure in the air rinse chamber is higher than the exhaust pressure in the infeed chamber.

3. The cap sterilizer according to claim 1, further comprising a washing chamber configured to wash the cap air-rinsed in the air rinse chamber, wherein the air rinse chamber is exhausted and an exhaust pressure in the washing chamber is higher than the exhaust pressure in the infeed chamber.

4. The cap sterilizer according to claim 1, wherein a conveying speed of the cap is 100 cpm or more and 1500 cpm or less.

5. A content filling system comprising the cap sterilizer according to claim 1.

6. A cap sterilization method comprising:
   feeding a cap from an infeed chamber to a sterilant atomizing chamber;
   spraying a sterilant against the cap in the sterilant atomizing chamber; and
   air rinsing the cap, sprayed with the sterilant in the sterilant atomizing chamber, in an air rinse chamber,
   wherein the infeed chamber, the sterilant atomizing chamber, and the air rinse chamber are arranged in this order along a conveying direction of the cap,
   at least the infeed chamber and the air rinse chamber are exhausted,
   an interior of the infeed chamber, an interior of the sterilant atomizing chamber and an interior of the air rinse chamber are maintained at a positive pressure, and
   an exhaust pressure in the infeed chamber and an exhaust pressure in the air rinse chamber are higher than an exhaust pressure in the sterilant atomizing chamber, or the sterilant atomizing chamber is not exhausted.

* * * * *